US005593666A

United States Patent [19]
McDonald

[11] Patent Number: 5,593,666
[45] Date of Patent: Jan. 14, 1997

[54] METHODS AND COMPOSITIONS FOR TREATING THROMBOCYTOPENIA

[75] Inventor: Ted P. McDonald, Knoxville, Tenn.

[73] Assignee: The University of Tennessee Research Corp., Knoxville, Tenn.

[21] Appl. No.: 330,517

[22] Filed: Oct. 27, 1994

Related U.S. Application Data

[63] Continuation-in-part of Ser. No. 291,376, Aug. 16, 1994, abandoned.

[51] Int. Cl.$^6$ .......................... A61K 45/05; A61K 38/00; C07K 1/00
[52] U.S. Cl. ........................ 424/85.1; 424/85.2; 530/351; 530/399; 530/830; 514/8; 514/12; 514/21
[58] Field of Search ................................ 424/85.1, 85.2; 530/351, 399, 830; 514/81, 12, 21

[56] References Cited

U.S. PATENT DOCUMENTS

| | | | |
|---|---|---|---|
| 4,894,440 | 1/1990 | Rosenberg | 530/351 |
| 5,128,449 | 7/1992 | McDonald | 530/351 |
| 5,155,211 | 10/1992 | Rosenberg | 530/351 |

OTHER PUBLICATIONS

Lok et al, Nature, vol. 369, pp. 565–567, 16 Jun. 1994.
De Sauvage et al., Nature, vol. 369, pp. 533–538, 16 Jun. 1994.
Carter et al, Radiation Research, vol. 135, pp. 32–39, 1993.
Foster et al, Proc. Natl. Acad. Sci. USA, vol. 91, pp. 13023–13027, Dec. 1994.
Bartley et al, Cell, vol. 77, pp. 1117–1124, Jul. 1, 1994.
Solina et al, FEBS Letters, vol. 353, pp. 57–61, 1994.
De Sauvage et al., Stimulation of Megakaryocytopoiesis and Thrombopoiesis by the c–Mpl Ligand. Nature 1994; 369:533–538.
Lok, et al., Cloning and Expression of Murine Thrombopietin cDNA and Stimulation of Platelet Production in vivo. Nature 1994; 369:565–567.
Kaushansky et al., Promotion of Megakaryocyte Progenitor Expansion and Differentiation by the Ligand Thrombopoietin. Nature 1994; 369:568–570.
Wendling et al., Promotion of Megakaryocyte Progenitor Expansion and Differentiation by the Ligand Thrombopoietin. Nature 1994; 369:571–574.
Sloand EM, Klein HG, Banks SM. Epidemiology of thrombocytopenia in HIV Infection. Eur J Haematol 1992; 48:168–172.
U.S. Department of Health and Human Services. 1993 Revised Classification System for HIV Infection and Expanded Surveillance Case Definition for AIDS Among Adolescents and Adults. Morbid Mortal Weekly Rep 1992; 41/ (RR–17):1–19.
Walsh CM, Nardi MA, Karpetkin S. On the Mechanism of Thrombocytopenic Purpura in Sexually Active Homosexual Men. N Eng J Med 1984; 311:635–639.
Bel-Ali Z, Dufour V, Najean Y. Platelet Kinetics in Human Immunodeficiency Virus Induced Thrombocytopenia. Am J Hematol 1987; 26:299–304.

Zucker–Franklin D, Termin CS, Cooper MC. Structural Changes in the Megakaryocytes of Patients Infected with the Human Immunodeficiency Virus (HIV–1). Am J Pathol 1989; 134:1295–1303.
Scadden DT, Zon LI, Groopman JE. Pathophysiology and Management of HIV–Associated Hematologic Disorders. Blood 1989; 74:1455–1463.
Zucker–Franklin D, Sermetis S, Zheng ZY, Internalization of Human Immunodeficiency Virus Type 1 and Other Retroviruses by Megakaryocytes and Platelets. Blood 1990; 75"1920–1923.
Najean Y, Rain JD. The Mechanism of Thrombocytopenia in Patients with HIV Infection. J Lab Clin Med 1994; 123:415–420.
Jolicoeur P. Murine Acquired Immunodeficiency Syndrome (MAIDS): An Animal Model to Study the AIDS Pathogenesis. FASEB J 1991; 5:2398–2405.
Morse HC, Chattopadhyay SK. Masahiko M, Frederickson TN, Hügin AW, Hartley JW. Retrovirus–Induced Immunodeficiency in the Mouse: MAIDS as a Model for AIDS. AIDS 1992; 6:607–621.
Mosier DE, Yetter RA, Morse HC. Retroviral Induction of Acute Lymphoproliferative Disease and Profound Immunosuppression in Adult C57BL/6 Mice. J Exp Med 1985; 161:766–784.
Chow FPR, Sutton PA, Hamburger AW. 3'–azido–3'–Deoxythymidine Ameliorates the Thrombocytopenia Observed in a Murine Model of AIDS. Exp. Hematol 1990; 18:1038–1041.
Chow FPR, Chen RB, Hamburger AW. Sustained Elevation of Platelet Counts by Long–Term Azidothymidine Treatment of Immunosuppressed Mice. J Lab Clin Med 1993; 121:562–569.
Chow FPR, Ordóñez JV, Sutton PA, Hamburger AW. Regulation of Megakaryocyte Colony Forming Cell Numbers and Ploidy by Dideoxynucleosides in Immunodeficient Mice. Am J Hematol 1993; 44:249–255.
McDonald TP, Clift RE, Cottrell MB. A Four–Step Procedure for the Purification of Thrombopoietin. Exp Hematol 1989; 17:865871.
McDonald TP. Bioassay for Thrombopoietin Utilizing Mice in Rebound Thrombocytosis. Proc Soc Exp Biol Med 1973; 144:1006–1012.
McDonald TP. A Comparison of Platelet Size, Platelet Count, and Platelet $^{35}$S incorporation as Assays for Thrombopoietin. Br J Hematol 1976; 34:257–267.

(List continued on next page.)

Primary Examiner—Elizabeth C. Weimar
Assistant Examiner—Abdel A. Mohamed
Attorney, Agent, or Firm—John F. Daniels, III

[57] ABSTRACT

A method and composition utilizing thrombopoietin for increasing platelet cell counts in thrombocytopenia is disclosed. The method and composition are suitable for treatments of patients suffering from medical conditions, such as HIV/AIDS or chemotherapy, which result in low platelet cell numbers. Also disclosed are the active moieties or domains of the thrombopoietin molecule.

27 Claims, 11 Drawing Sheets

OTHER PUBLICATIONS

Cullen WC, McDonald TP. Comparison of Sterologic Techniques for the Quantification of Megakaryocyte Size and Number. Exp Hematol 1986; 14:782–788.

Bauer S, Khan A, Klein A, Starasoler L. Naked Megakaryocyte Nuclei as an Indicator of Human Immunodeficiency Virus Infection. Arch Pathol Lab Med 1992; 116:1025–1029.

Levin J, Bessman JD. The Inverse Relation Between Platelet Volume and Platelet Number. J Lab Clin Med 1983; 101:295–307.

McDonald TP, Clift RE, Cottrell MB. Large, Chronic Doses of Erythropoietin cause Thrombocytopenia in Mice. Blood 1992; 80:352–358.

Chow FPR, Zsebo K. Hamburger AW. Effects of *in vivo* Administration of Stem Cell Factor on Thrombopoiesis in Normal and Immunodeficient Mice. Exp Hematol 1993; 21:1255–1262.

Carter CD and McDonald TP. Thrombopoietin from Human Embryonic Kidney Cells Causes Increased Thrombocytopoiesis in Sublethally Irradiated Mice. Radiat. Res 1992; 132:74–81.

Carter CD, Shultz TW, McDonald TP. Thrombopoietin From Human Embryonic Kidney Cells Stimulates an Increase in Megakaryocyte Size in Sublethally Irradiated Mice. Radiat Res 1993; 135:32–39.

McDonald, TP. Thrombopoietin Its Biology, Clinical Aspects, and Possibilities. The Amer. J. of Ped. Hem./Onc. 1992; 14(1):8–21.

McDonald, et al.. Thrombopoietin from Human Embryonic Kidney Cells is the Same Factor as C–mpl–ligand. Blood 1994 (in press).

Sakaguichi M, Sato T and Groopman JE. Human Immunodeficiency Virus Infection of Megakaryocytic Cells. Blood 1991; 77:481–485.

McDonald TP, Cottrell M, Clift R. Effects of Short–Term Hypoxia on Platelet Counts of Mice. Blood 1978; 51:165–175.

McDonald TP, Cottrell M, Swearingen C, Clift R. Comparative Effects of Thrombopoietin and Interleukin—6 on Murine Megakaryocytopoiesis and Platelet Production. Blood 1991; 77:735–740.

```
                                                                                    tcttcctaccatctgctcccagagggctgcctgctgtgcacttgggtcctgcctggggccctttctccaccggatagattcctcaccttggcccgcctttg cccaccctactctgcccagaagtgcaagagcctaagccgcctccatggcccaggaaggattcaggggagaggcccaaacagggagcacgccagcca
                                                                                                               -20                        -10                                              ●
                                                                                                               MetGluLeuThrGluLeuLeuLeuValMetLeuLeuLeuLeuThrAlaArgLeuThrSerProAlaProProAlaCysAsp
                                                                                                               ATGGAGCTGACTGAATTGCTCCTGGTGTCATGCTCCTGCTTCTCCAACTGCTTCCCAGCCTGTCCAAGGCTAACGCTGTCCAGCCCGGCTCCTGCTGTTG
```

| FIG. 9A |
|---------|
| FIG. 9B |

```
                180                                                    190                                                    200
ProAsnArgThrSerGlyLeuLeuGluThr AsnPheThr AlaSerAlaArgThrThrGlySerGlyLeuLeuLysTrpGlnGlnGlyPheArgAlaLysIle
CCAAACAGGACTTCTGGATTGTTGGAGACAAACTTCACTGCCTCAGCCAGAACTACTGGCTCTGGGCTTCTGAAGTGGCAGCAGGATTCAGAGCCAAGA
           210                                                    220                                                    230
ProGlyLeuLeuAsnGlnThrSerArgSerLeuAspGlnIleProGlyTyrLeuAsnArgIleHisGluLeuLeu AsnGlyLeu ArgGlyLeuPhePro
TTCTGGTCTCTGCTGAACCAAACCTCCAGGTCCCTGGACCAAATCCCCGGATACCTGAACAGGATACACGAACTCTTGAATGGAACTCGTGGACTCTTTCC
                               250                                                    260                                                    270
GlyProSerArgArgThrLeuGlyAlaProAspIleSerSerSerGlyThrGlySerAspThrGlnAsnLeuGlnProProAsnLeuProProGlyTyrSerProSer
TGGACCCTCACGCAGGAGGACCCTCAGGAGCCCTAGGAGACATTTCCTCAGGAACATCAGACACAGGCTCCCGCCACCAACCTCCAGCCTCCCAACCCTGGATATTCCCTTCC
                               280                                                    290                                                    300
ProThrHisProProThrGlyGlnTyrThrLeuProThrLeuPheProLeuProThrGlyGlnLeuHisProLeuProAspProSerProSer
CCAACCCATCCTACTGGACAGTATACGCTCTTCCACCGGACTCTTCCCACCTTGCCCACCTTGTCCAGTCCAGCCCTCCACCCCCTGCTTCCTGACCCTTCTG
                               310                                                    320                                                    330
ProThrProProThrSerProLeuLeuLeuLeuAsnThrSerTyrThrHisSerGln AsnLeuSer GlnGluGly
CTCCAACGCCACCCTACCAGCCTCTCTAAACACATCCTACACCCACTCCCAGAATCTGTCTCAGGAAGGGTAAggttctcagacactgccgacatc
agcattgtctcatgtacagctcccttccctgcagggcgccctgggagcaactggacaagatttttcctactttcctgaaaccaaagccctggtaaaa
gggatacacaggactgaaaagggaatcattttcactgtacattataaacctcacatgattctcacatgtcttttctgtgataactctgcaaaggcttgggctggcctggcagtt
gctctttggtctatttttctgcagaatttgcagaaatttcaaatttcaaatccactgattctcaaatccttttgcttgaatcctgcaaaggcttcaacgccccccatcccctttactat
gaacagagggagacttaacctttgagtcagaaaacagaaaagggtaattttcctttactcttgagaaatgaataagcttttctctcagaaaaaaaaaaaaaaaa
cattctcagtgggaccttgatcccatattctctaacagatctttttactcttgagaaatgaataagcttttctctcagaaaaaaaaaaaaaaaaaaaa
```

*FIG. 9B*

TABLE I

| TREATMENT | AVERAGE NUMBER OF NAKED NUCLEI PER HPF | $p$ |
|---|---|---|
| CONTROL | 0.26 ± 0.09 | — |
| 3 WEEKS PI | 0.54 ± 0.07 | 0.04 |
| 8 WEEKS PI | 0.05 ± 0.04 | 0.07 |

*FIG. 10*

METHODS AND COMPOSITIONS FOR TREATING THROMBOCYTOPENIA

CROSS-REFERENCE TO RELATED APPLICATIONS

This is a continuation in-part of U.S. patent application Ser. No. 08/291,376, filed Aug. 16, 1994 now abandoned.

FIELD OF THE INVENTION

This invention relates to therapies employing thrombopoietin, and especially those which include the treatment of thrombocytopenia in immunodeficient and chemotherapy patients.

BACKGROUND

Thrombopoietin (TPO) protein, a cytokine, stimulates the creation and maturation of megakaryocytes. TPO is also referred to as thrombocytopoiesis-stimulating factor (TSF). TPO plays a major role in stimulating thrombocytopoiesis (platelet production). For a comprehensive review of TPO, see McDonald, The Amer. J. of Ped. Hem./Onc. 14 (1): 8–21 (1992), which is incorporated herein by reference. All references cited are incorporated hereinby reference.

Platelets are the blood cells responsible for clotting and low platelet counts can lead directly to excessive internal bleeding. Platelets—small blood cell fragments that break off from a relatively huge parent cell (the megakaryocyte)—are key to normal blood clotting. They routinely serve as patches for small defects in blood vessels to confine hemorrhage and encourage ordinary coagulation. Vast numbers of platelets aggregate to form a thrombus that stops excessive bleeding at wound sites.

In thrombocytopenia, blood platelet levels drop and cause abnormal bleeding into the skin, especially from small blood vessels. This is a serious and sometimes fatal condition. Thrombocytopenia is one of the most serious side effects of chemotherapy and irradiation. Thrombocytopenia also may result from infectious disease, leukemia, bone marrow transplants, certain diseases of the spleen, complications of pregnancy and child-bearing, gram-negative sepsis, complications of cardiac surgery, aplastic anemia and myelodysplastic syndromes.

With regards to chemotherapy, as many as 250,000 patients undergo such treatment each year in the United States alone, according to the FDA. Of those, 35% experience either severe or moderately severe thrombocytopenia. Last year, a total of about 10 million platelet transfusions were performed in the United States to enhance the blood's ability to clot.

Such platelet transfusions carry inherent risks of causing an immune response to the foreign platelets, transmitting viral diseases, such as HIV and hepatitis, and causing graft-vs-host disease and congestive heart failure.

TPO, by stimulating production of the body's own platelets, has the potential to restore platelet counts to near-normal levels in these patients. If platelets could be maintained at normal levels by administering TPO, it may be possible to provide patients with higher and potentially curative doses of standard cancer drugs without the limiting side effects.

Thrombocytopenia is also an important complication of infection with Human Immunodeficiency Virus Type-I (HIV-1). While HIV-related thrombocytopenia (HRT) may appear at any stage of HIV infection, the incidence of HRT appears to range from around 9% in HIV-infected, non-AIDS patients to around 21% in HIV infected patients with AIDS. Severity of thrombocytopenia has been correlated with the stage of the disease. See, Sloand, et al, *Eur J Hematol*, 48:168–172 (1992). HRT is a significant clinical problem, e.g., 40% of patients have platelet concentrations below 50,000/μl and suffer bleeding episodes as a result, and 1 of 1004 patients in one study died as a result of intracranial hemorrhage. HRT is considered to be a Category B clinical condition in the CDC classification system for HIV infection. See, U.S. Dept. of Health, et al, *Morbid Mortal Weekly Rep*, (RR-17): 1–19 (1992).

The mechanism of thrombocytopenia in HIV infection has been the subject of considerable debate. It now seems clear that multiple mechanisms contribute to the clinical entity of HRT. HRT has been attributed to an autoimmune mechanism, supported by a common finding of elevated platelet-bound immunoglobulin G, and decreased platelet lifespan. See, Walsh, et al, *N Eng J Med*, 311:635–639 (1984); Ben-Ali, et al, *Am J Hematol*, 26:299–304 (1987). On the other hand, a defective production of platelets has also been proposed as a mechanism, supported by findings of morphological and quantitative abnormalities of megakaryocytes in the bone marrow of HIV- infected individuals. See, Zucker-Franklin, et al, *Am J Pathol*, 134:1295–1305 (1989); Scadden, et al, *Blood*, 1455–1463 (1989). Further, megakaryocytes internalize HIV-I viruses in the bone marrow. See, Zucker-Franklin, et al, *Blood*, 77:481–485 (1990). More recently, it has been suggested that the immune-mediated mechanism of platelet destruction is more important in early, asymptomatic HIV infection, whereas platelet-production defects predominate in later-stage patients with AIDS-related complex (ARC) or AIDS. See, Najean, et al, *J Lab Clin Med*, 123:415–420 (1994).

Murine leukemia virus infection in mice is well-recognized as a model for HIV-infection. See, Jolicoeur, *FASEB J*, 5:2398–2405 (1991); Morse, et al, *AIDS*, 6:607–621 (1992). This mouse model has been termed murine acquired immunodeficiency syndrome (MAIDS). The LP-BM5 murine leukemia virus (MuLV) is actually a mixture of ecotropic and mink cell focus forming MuLVs, which causes a lymphoproliferative disease in mice which is typified by lymphadenopathy, splenomegaly, and immunosuppression. See, Chow, et al, *Exp. Hematol*, 18:1038–1041 (1990). MAIDS has also been used as a model for HRT by examining the effects of azidothymidine (AZT) on platelet counts. In these studies, platelet counts typically fell to approximately 80% of control values, and were increased by therapy with AZT. See, Chow, et al, *Exp. Hematol*, 18:1038–1041 (1990); Chow, et al, *J Lab Clin Med*, 121:562–569 (1993); Chow, et al, *Am J Hematol*, 44:249–255(1993).

The use of AZT in humans, as has been widely reported, is not without significant risk of serious side effects. The risk of these side effects increases with increasingly higher dosages of AZT required to combat HIV/AIDS infections and raise platelet counts.

Particularly, then, there exists a serious and urgent need for a method and composition for treatment of HIV/AIDS-related thrombocytopenia, to raise platelet cell counts in such patents. Such method and composition would also advantageously reduce the need to use AZT to raise platelet counts in HIV/AIDS-infected patients.

More generally, there remains an urgent and unfulfilled need for a method and composition for the treatment of various thrombocytopenia-related conditions, such as result from the side effects of chemotherapy and irradiation in cancer patients, as well as other conditions described above, which would advantageously eliminate the need for risky platelet transfusions.

With respect to the structure of the human TPO molecule, TPO consists of 332 amino acid residues with a leader sequence of 21 amino acid residues. At residues 153 and 154, there is an Arg-Arg sequence, which is a degradation point. It has been reported that the first half of this molecule up to residue 153, which is the N-terminal region of the TPO molecule, has the same TPO activity as the whole molecule. This is based on the results that both the full-length and N-terminal fragment of TPO stimulated BaF$_3$/mpl cell in vitro. In this assay, supernatants from HEK 293 cells transfected with the sequence for the N-terminal domain had activity similar to that of supernatants from HEK 293 cells expressing the full-length TPO. See de Sauvage et al, *Nature*, 369:533–538 (1994).

The N-terminal fragment has been characterized as the erythropoietin-like (EPO-like) domain of TPO. Thus, it is disclosed in the de Sauvage publication that the EPO-like domain (N-terminal portion) is the mature or active moiety of TPO responsible for increasing platelet cell counts. In the de Sauvage publication, page 537, it states that the importance of the C-terminal region of the TPO molecule, which encompasses that portion from the Arg residue at amino acid position 154 to the end of the sequence, is unknown and remains to be elucidated. It is suggested that this region may act to stabilize and increase the half-life of circulating TPO. There is no suggestion in the de Sauvage publication that the C-terminal region or any portion of that region possesses any TPO activity.

As disclosed by de Sauvage, the C-terminal domain of TPO is not required for binding and activation of the c-Mpl receptor, which is the cytokine receptor for the active TPO moiety or ligand and which regulates megakaryocytopoiesis.

Further, it has been reported with regards to murine TPO that the junction between the N-terminal EPO-like domain and the C-terminal domain also contains a pair of arginine residues resembling a dibasic proteolytic site. It is disclosed that there is no evidence at this time to suggest that the recombinant c-Mpl ligand (TPO) produced in baby hamster kidney (BHK) cells is cleaved at this site to form the N- and C-terminal fragments. Lok et al, *Nature*, 369:565–568 (1994).

It would therefore certainly be a surprising and unexpected discovery if the C-terminal portion of the TPO molecule were found to be a moiety or ligand more active than the N-terminal domain for the therapeutic effect of advantageously increasing or raising platelet cell counts in thrombocytopenic patients.

SUMMARY OF THE INVENTION

The present invention provides methods for therapeutically treating thrombocytopenia by administering to a patient a dose of thrombopoietin, or its active fragments thereof, such as the N- or C-terminal fragments, with a pharmaceutically acceptable carrier. The methods of the present invention are sufficient to increase platelet cell counts by at least about 20% within about 2 to 4 days after administration of the dose of thrombopoietin. These therapies advantageously and unexpectedly address and provide a solution for the above-described unfulfilled needs.

The TPO utilized in the present invention is substantially free from other human proteins. TPO may be purified from cell sources producing the protein naturally or upon induction with other factors. TPO may be produced by recombinant genetic engineering techniques. TPO may also be synthesized by chemical techniques, or a combination of the above-listed techniques.

Accordingly, an aspect of the present invention provides for pharmaceutical compositions containing a therapeutically effective amount of homogeneous naturally-derived, chemically-derived or recombinant TP0, or an effective amount of one or more active peptide fragments thereof. These pharmaceutical compositions may be employed in methods for treating disease states or disorders characterized by a deficiency of platelets. The TPO compositions of the present invention may be advantageously used to treat blood disorders such as thrombocytopenia.

Thus, the TPO compositions of the present invention or pharmaceutically effective fragments thereof may be employed in the treatment of patients with poor platelet production capabilities. The compositions augment production of platelets in patients having impaired platelet production (such as HIV/AIDS patients or patients undergoing cancer chemotherapy). The TPO compositions of the present invention may be also used as an adjunctive therapy for bone marrow transplant patients.

The therapeutic methods of the invention may further advantageously include administering simultaneously, or sequentially, either before or after TPO or one or more peptide fragments thereof, an effective amount of at least one other hematopoietic factor such as erythropoietin (EPO), granulocyte colony stimulating factor (G-CSF), granulocyte-macrophage colony stimulating factor (GM-CSF), interleukins, growth factor, or an antibody to advantageously influence other hematopoietic conditions. Such particularly suitable factors are EPO, GM-CSF, and G-CSF, which are the other primary stimulating factors for red and white blood cells.

The methods and compositions of the present invention are unexpectedly and advantageously suitable for moderating or ameliorating thrombocytopenia in cancer and AIDS patients, for accelerating the regeneration of self-supporting platelet levels in BMT patients, for moderating the thrombocytopenia that precedes and complicates graft rejection, for treating patients with myelodysplastic diseases, and for reversing or improving the thrombocytopenia seen in more than half of the patients with chronic renal disease.

The methods and compositions of this invention therefore unexpectedly and surprisingly provide for increasing platelet cell counts above a baseline count by at least about 20% or greater in such compromised patients. Such an increase represents a significant and unexpected clinical advance in the treatment of thrombocytopenia.

With respect to the fragments of the TPO molecule, it has now been surprisingly discovered that both the N-terminal and C-terminal fragments of TPO are active in stimulating platelet cell increases.

It has now been further surprisingly and unexpectedly discovered that the C-terminal fragment is that portion of the TPO molecule which is the more active moiety for advantageously increasing platelet cell counts. This is surprising and unexpected in view of the above discussed publications, which conclude that the N-terminal fragment is the active TPO moiety, and that the role of the C-terminal fragment has not yet been elucidated.

Accordingly then, an unexpected and surprising aspect of the present invention is a therapeutic composition which is comprised of a therapeutic amount of the C-terminal fragment of TPO and a pharmaceutically acceptable carrier. A therapeutic amount of the C-terminal fragment is defined as that amount sufficient to unexpectedly increase platelet cell counts in a thrombocytopenic patient by at least about 20% above a baseline count. This unexpected increase in platelet counts occurs within about 2 to 4 days after administration of the C-terminal fragment.

With regards then to increasing platelet cell counts in a patient in need thereof, the present invention further advantageously provides a method of administering to the patient the composition comprised of the therapeutic amount of the C-terminal fragment and the pharmaceutically acceptable carrier. The composition may be administered in an amount and for a time sufficient to increase platelet cell counts to normal or near-normal numbers in a thrombocytopenic patient.

While less active than the C-terminal fragment in raising platelet cell counts, the present invention further provides compositions and methods of administering the N-terminal fragment of TPO.

The therapeutic compositions and methods of the present invention may further advantageously include an effective amount of at least one other hematopoietic factor such as erythropoietin (EPO), granulocyte colony stimulating factor (G-CSF), granulocyte-macrophage colony stimulating factor (GM-CSF), interleukins, growth factor or an antibody to advantageously influence other hematopoietic conditions. Such particularly suitable factors are EPO, GM-CSF, and G-CSF, which are the other primary stimulating factors for red and white blood cells.

The present results unexpectedly and surprisingly demonstrate that even a partially-purified preparation of C-terminal fragment is about 3 to 8 fold more active in increasing platelet cell counts than the recombinant whole TPO molecule or N-terminal fragment of the TPO, as reported in the de Sauvage publication. The purified preparation, furthermore, is advantageously many fold more active than any TPO preparation heretofore reported, including the recombinant forms.

The compositions and methods of the present invention therefore represent an unexpected and significant advance towards fulfilling the long-felt need in the art for treating a variety of thrombocytopenic conditions. These conditions, as described above, include but are not limited to the treatment of thrombocytopenia in chemotherapeutic and HIV/AIDS patients.

Other aspects and advantages of the present invention will be readily apparent upon consideration of the following detailed description, including the drawings described hereinafter, and the appended claims.

BRIEF DESCRIPTION OF THE DRAWINGS

The present invention will be more readily appreciated in connection with the accompanying drawings in which:

FIGS. 9A and 9B show the nucleotide sequence and deduced amino-acid sequence of human TPO cDNA. Nucleotides are numbered at the beginning of each line. Amino acids are numbered above the sequence starting at Ser 1 of the mature TPO protein sequence. The 5' and 3' untranslated regions are indicated in lower case numbers. The boundaries of the exon contained in a 390-bp EcoRI-XbaI fragment from a human genomic DNA library are indicated by arrows and the potential N-glycosylation sites are boxed. Cysteine residues are indicated by a dot above the sequence. The underlined sequence corresponds to the N-terminal sequence determined by protein sequencing of pig TPO.

Table 1, FIG. 10 shows the average number of naked megakaryocyte nuclei per 400×field in femoral marrow of mice post infection with murine leukemia virus.

DETAILED DESCRIPTION OF THE INVENTION

Figure 1:
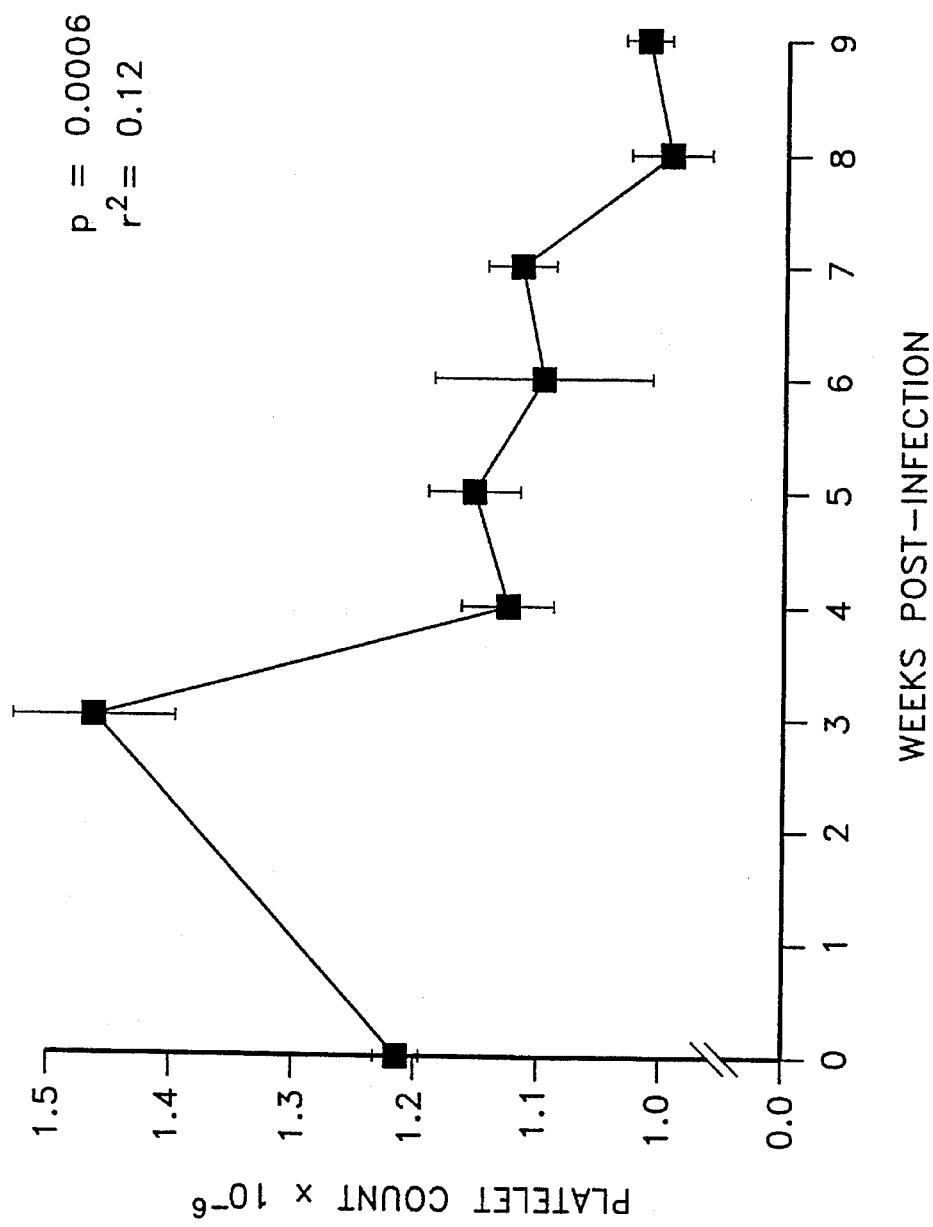
FIG. 1 shows platelet counts of mice in the weeks following infection with murine leukemia virus. Mice represented on Day 0 are pooled controls, injected with Dulbecco's Media and sacrificed on the same analysis days as the infected mice. Data are expressed as mean±S.E. Total number of mice in the analysis was 94.

The novel methods and compositions of the present invention utilize TPO or active fragments thereof. These active fragments include the N-terminal portion of TPO and, more particularly, the C-terminal fragment. It should be understood that reference hereinafter to TPO includes the entire protein or the active fragments of thereof. TPO is a homogeneous or purified protein substantially free from association with other human proteinaceous materials. TPO can be produced via recombinant techniques. Such techniques enable large quantity production of pure, active TPO useful for therapeutic applications. Alternatively, TPO may be obtained as a homogeneous protein purified from a mammalian cell line secreting or expressing it, such as a human embryonic kidney cell line (HEK). Further TPO may be chemically synthesized. The TPO utilized in the present invention has been biochemically characterized in detail in U.S. Pat. No. 5,128,499 (McDonald), which is incorporated herein by reference.

Briefly, purified TPO is preferably characterized by the following biochemical and biological properties as described in U.S. Pat. No. 5,128,449:

(1) has a molecular weight as determined by SDS-PAGE of about 15,000 daltons as a monomer, and about 30,000 daltons as a dimer;

(2) has a specific activity of at least about 21,000 units/ mg, wherein a unit of specific activity is determined by dividing one milligram by the weight of TPO required to increase the percent $^{35}$S incorporation into platelets of mice by 50 percent above control baseline in an immunothrombocythemic mouse assay. This widely used and well-recognized assay assesses the in vivo capacity of an agent to enhance platelet release during the platelet rebound period following acute anti-platelet antibody-induced thrombocytopenia;

(3) is stained by Coomassie blue.

The TPO utilized in the present invention stimulates proliferation of the MO-7E cell line, which cell line is factor-dependent and expresses a high level of c-Mpl receptor (c-Mpl-R) on its surface. The MO-7E cell proliferation assay is essentially the same assay as the mpl-dependent BaF3/mpl cell proliferation assay. This shows that the TPO utilized in the present invention binds c-Mpl-R and stimulates proliferation of a mpl-dependent cell line.

Other results indicate that mRNA for the c-Mpl-ligand (TPO) may be isolated from HEK cells, and that cultured HEK cells produce a factor that stimulates BaF3/mpl cells (McDonald et al., (Blood), 1994 in press).

These results clearly demonstrate that the protein utilized in the present invention is indeed the long sought-after TPO.

The nucleotide sequence of human TPO consists of 1,774 nucleotides followed by a poly (A)$^+$ tail (SEQ ID NO: 1), as shown in FIG. 9, and as described in the de Sauvage publication. It defines an open reading frame of 1,059 nucleotides, which predicts a primary translation product of 353 amino acids (SEQ ID NO: 2). Flanking the open reading frame are 215 nucleotides of 5' and 498 nucleotides of 3' untranslated sequences. The mature human TPO polypeptide is comprised of 332 amino acids. An N-terminal fragment or domain thereof encompasses amino acid residues 1–153, and the C-terminal fragment or domain encompasses residues 154–332. The N-terminal fragment of, the predicted amino-acid sequence is highly hydrophobic and probably represents a signal peptide. Computer analysis indicates a potential cleavage site for signal peptidase between residues 21 and 22 of the primary translation product. Cleavage there would generate the mature polypeptide of 332 amino acids.

Comparison of the TPO sequence with the Genbank sequence database revealed 23% identity between the N-terminal 153 residues of TPO and EPO. When conservative substitutions are taken into account, this N-terminal region of TPO shows 50% similarity to EPO. Hence, the N-terminal portion of TPO has been referred to as the EPO-like domain.

At residues 153–154, there is a dibasic proteolytic cleavage site consisting of Arg-Arg residues. This site is readily cleaved, which produces the N-terminal EPO-like domain and the C-terminal domain.

With regards to the C-terminal domain, there are six potential sites for N-linked glycosylation. It is likely then that this domain is glycosylated. This C-terminal domain of 179 amino acids in length corresponds particularly well in size with a molecular weight of 15 kD, as described in U.S. Pat. No. 5,128,499 (McDonald) for the monomer of TPO. This 15 kD fragment readily self-associates under appropriate conditions to the active 30 kD TPO dimer. By way of previous results, it was shown that this 30 kD dimer possesses no EPO or EPO-like activity.

While the N-terminal fragment of TPO possesses some activity with regards to increasing numbers of platelets, it has now been unexpectedly and surprisingly discovered that the C-terminal fragment is the more active moiety or ligand of the TPO molecule. This moiety or ligand binds the c-Mpl receptor, which is the receptor for TPO. It is the C-terminal fragment then that unexpectedly stimulates the observed increase in platelet cell counts in the MAIDS animal model described hereinafter.

The biological activity of the C-terminal fragment of the TPO of the present invention of substantially increasing platelet cell counts is demonstrated by its ability to stimulate platelet cell production in vivo in thrombocytopenic mice infected with murine leukemia virus (LP-BM5). This mouse model (MAIDS) is correlated with the thrombocytopenia observed in HIV/AIDS patients, and is therefore believed to be predictive of efficacious treatments for increasing platelet counts in such patients, as well as other conditions inducing thrombocytopenia.

With regards to this animal model, male C57/BL mice were inoculated with 5×10$^4$ infectious particles of both ecotropic and mink cell focus-forming murine leukemia virus (MuLV) by a single intraperitoneal injection.

Sensitive indices of platelet production (percent $^{35}$S incorporation into platelets, platelet size, platelet count, and megakaryocyte size and number) were then evaluated over a period of 3–9 weeks post-infection (PI). Additionally, concentrations of platelet-associated immunoglobulins (PAIgG) were measured at the same time periods.

TPO partially-purified from HEK cells was administered to mice 9 weeks PI, and similar indices of platelet production, as described above, were measured 2,3, and 4 days after treatment with TPO.

Infected mice developed generalized lymphadenopathy and splenomegaly as previously described. See, Chow, et al, *Exp. Hematol*, 18:1038–1041 (1990). No changes in body weight were observed following infection, and no deaths of infected mice occurred. Hematocrits decreased following infection, falling to 92% of control values on week 9 P<0.005, data not shown).

Figure 2:
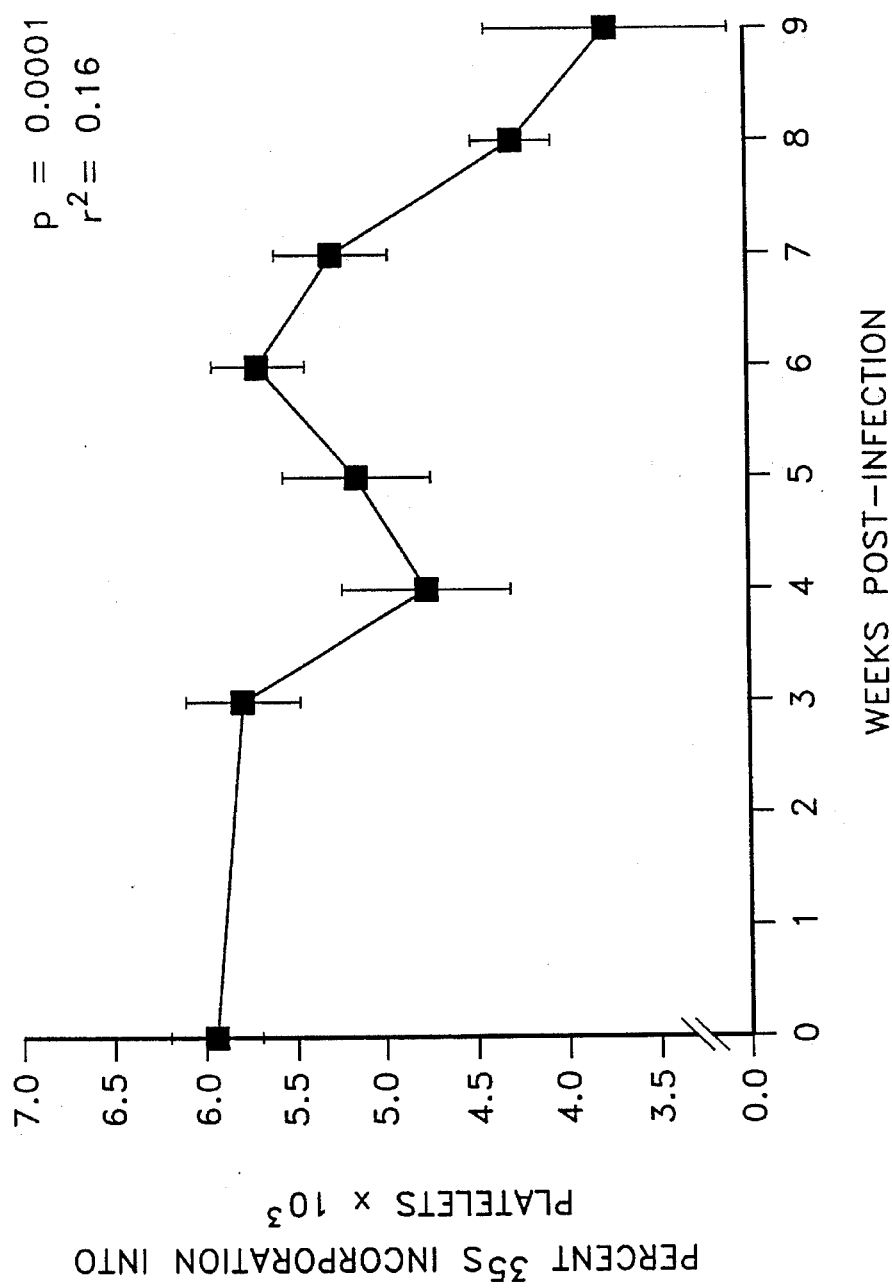
FIG. 2 shows-percent $^{35}$S incorporation into platelets of mice in the weeks following infection with murine leukemia virus. Mice represented on Day 0 are pooled controls, injected with Dulbecco's Media and sacrificed on the same analysis days as the infected mice. Data are expressed as mean±S.E. Total number of mice in the analysis was 85.
Figure 3:
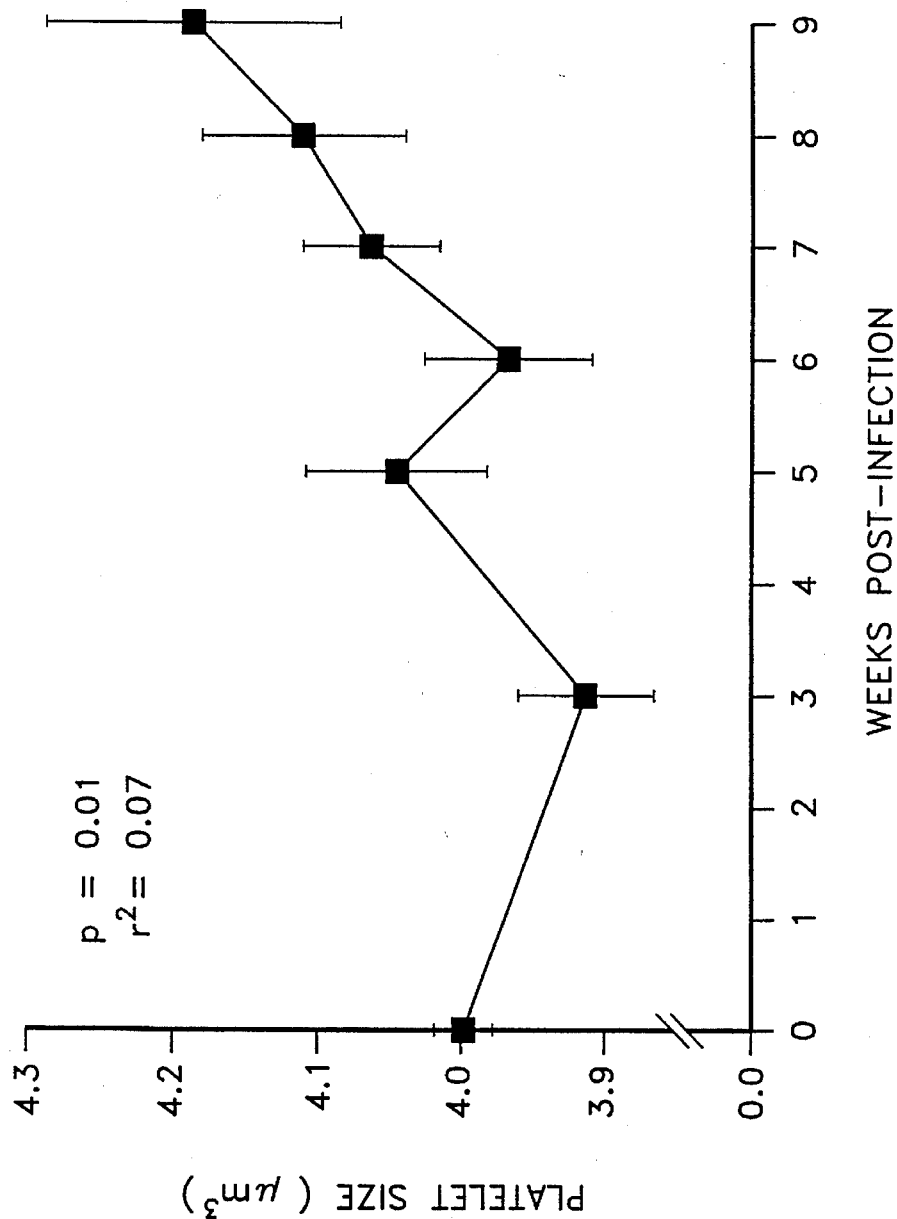
FIG. 3 shows mean platelet size of mice in the weeks following infection with murine leukemia virus. Mice represented on Day 0 are pooled controls, injected with Dulbecco's Media and sacrificed on the same analysis days as the infected mice. Data are expressed as mean±S.E. Total number of mice in the analysis was 89.

Platelet counts of infected mice decreased in a time-dependent fashion (P=0.0006, see FIG. 1). At 3 weeks PI, platelet counts in thrombocytopenic mice were significantly elevated over non-infected control mice (1.217 vs 1.460× 10$^6$/μl, P<0.0005). At the nadir of platelet count at 8 weeks, infected mice had platelet counts which were 82% of control values on week 9 (1.217 vs 0.998×10$^6$/μl ). Similarly, percent 35S incorporation into platelets decreased with time PI (P=0.0001, see FIG. 2), reaching levels which were 62% of control mice at 9 weeks PI (5.95 vs 3.73×10$^{-3}$). During the same period, platelet size of affected mice increased in a time-dependent fashion (P=0.01, see FIG. 3).

Levels of platelet bound IgG did not change over the 9 week study period (data not shown).

Figure 4:
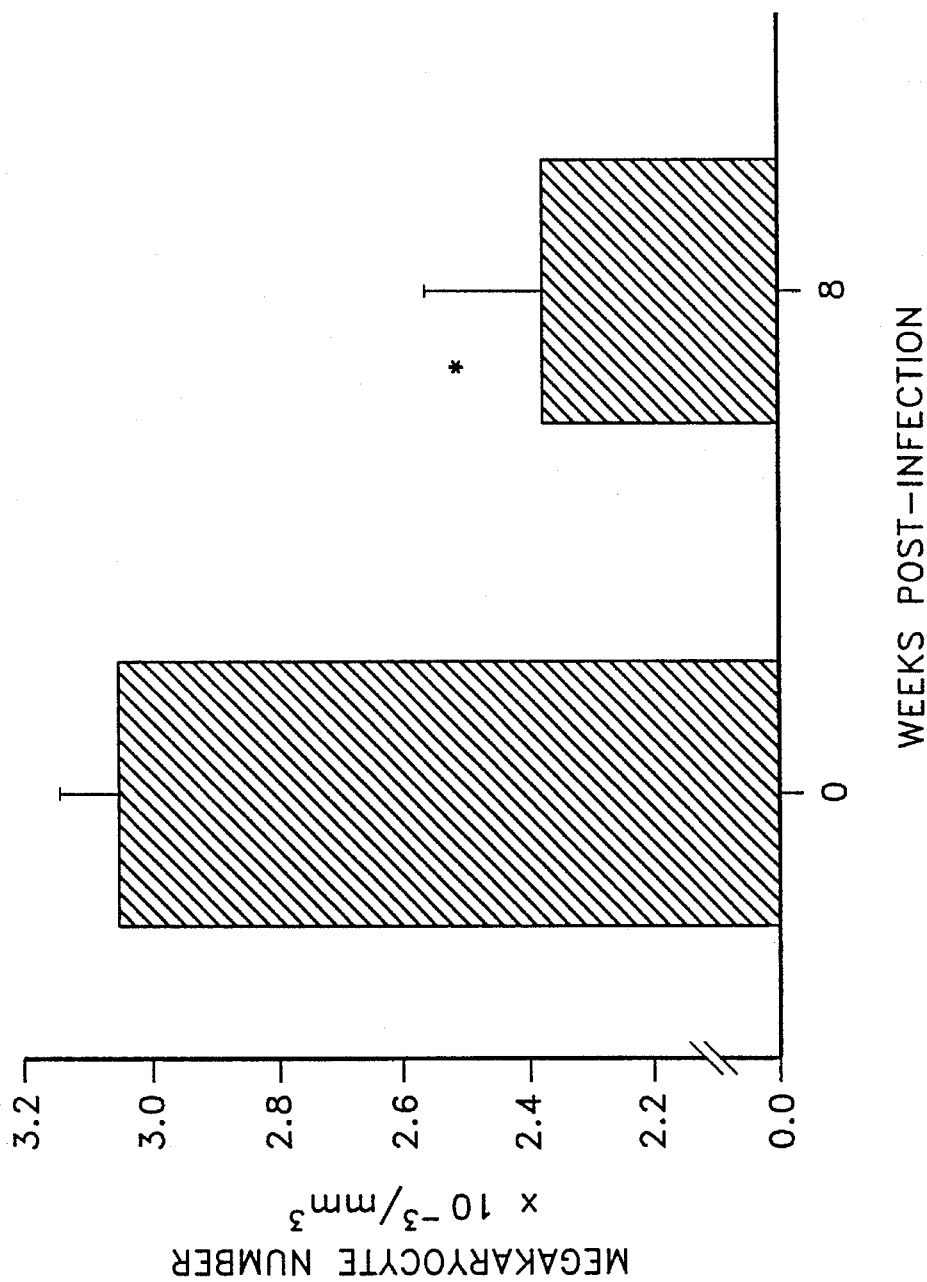
FIG. 4 shows mean number of megakaryocytes per mm$^3$ of femoral marrow of mice before and 8 weeks following infection with murine leukemia virus. Mice represented on Day 0 were injected with Dulbecco's Media and sacrificed on the same analysis day as the infected mice. Data are expressed as mean±S.E. Total number of mice in the analysis was 8. * Means were different by Student's $t$ test, p=0.02.
Figure 5:
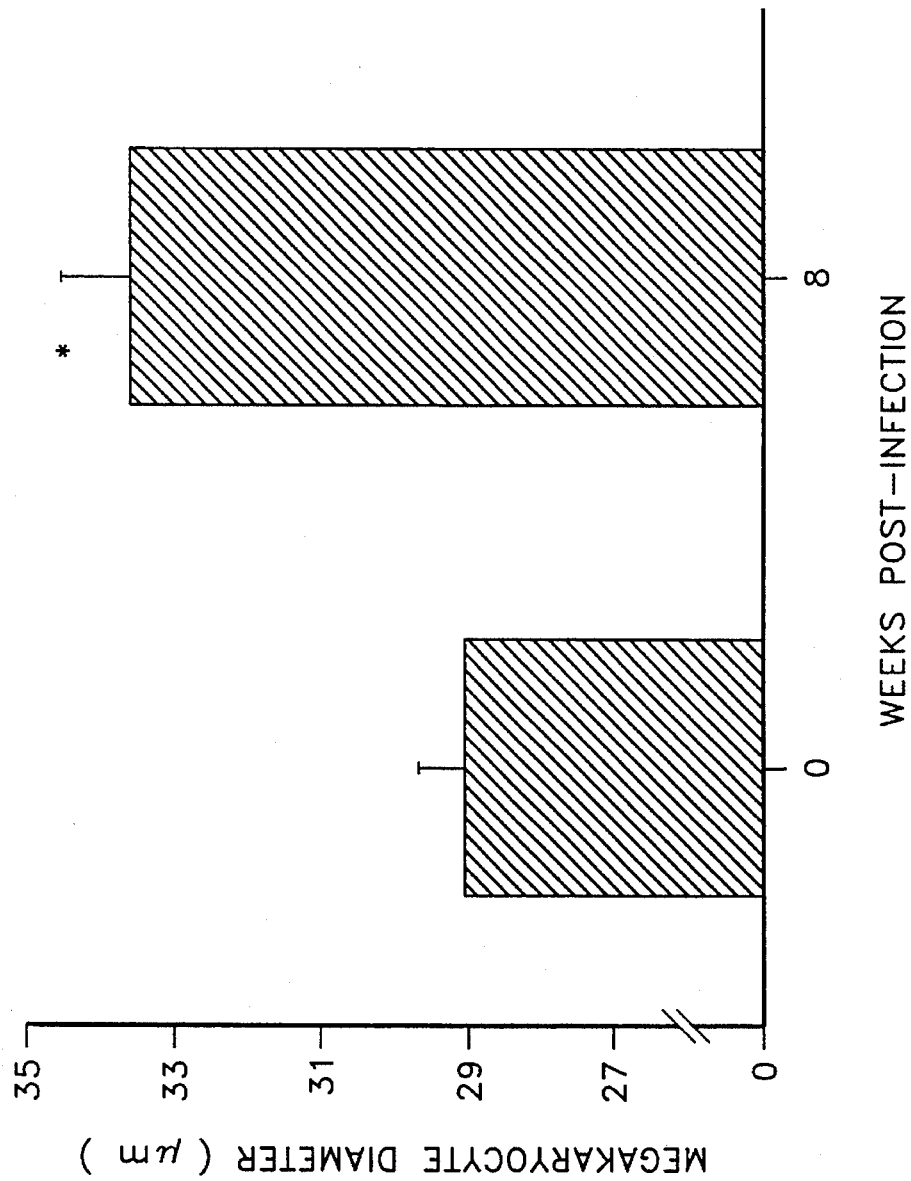
FIG. 5 shows mean diameter of megakaryocytes in femoral marrow of mice before and 8 weeks following infection with murine leukemia virus. Mice represented on Day 0 were injected with Dulbecco's Media and sacrificed on the same analysis day as the infected mice. Data are expressed as mean±S.E. Total number of mice in the analysis was 8. * Means were different by Student's $t$ test, p=0.007.

With regards to the precursor cell of platelets, megakaryocyte numbers were significantly decreased at 8 weeks PI (P=0.02, see FIG. 4), whereas mean megakaryocyte size increased during the same time period (P=0.007, see FIG. 5). Numbers of naked megakaryocyte nuclei were increased 3 weeks PI, but were not different from controls at 8 weeks PI (see Table I).

Table I shows the average number of naked megakaryocyte nuclei per 400×field in femoral marrow of mice post infection (PI) with murine leukemia virus. Mice represented as control were treated with Dulbecco's medium, and were sacrificed on the same analysis days as the infected mice. Data are expressed as mean±S.E. Each treatment group contained 4 mice. P-values indicated are from the Student's t test.

Table I shows that numbers of naked megakaryocyte nuclei were increased three weeks PI (P=0.04, Table I); however, naked nuclei were reduced eight weeks PI (P=0.07, Table I).

Figure 6:
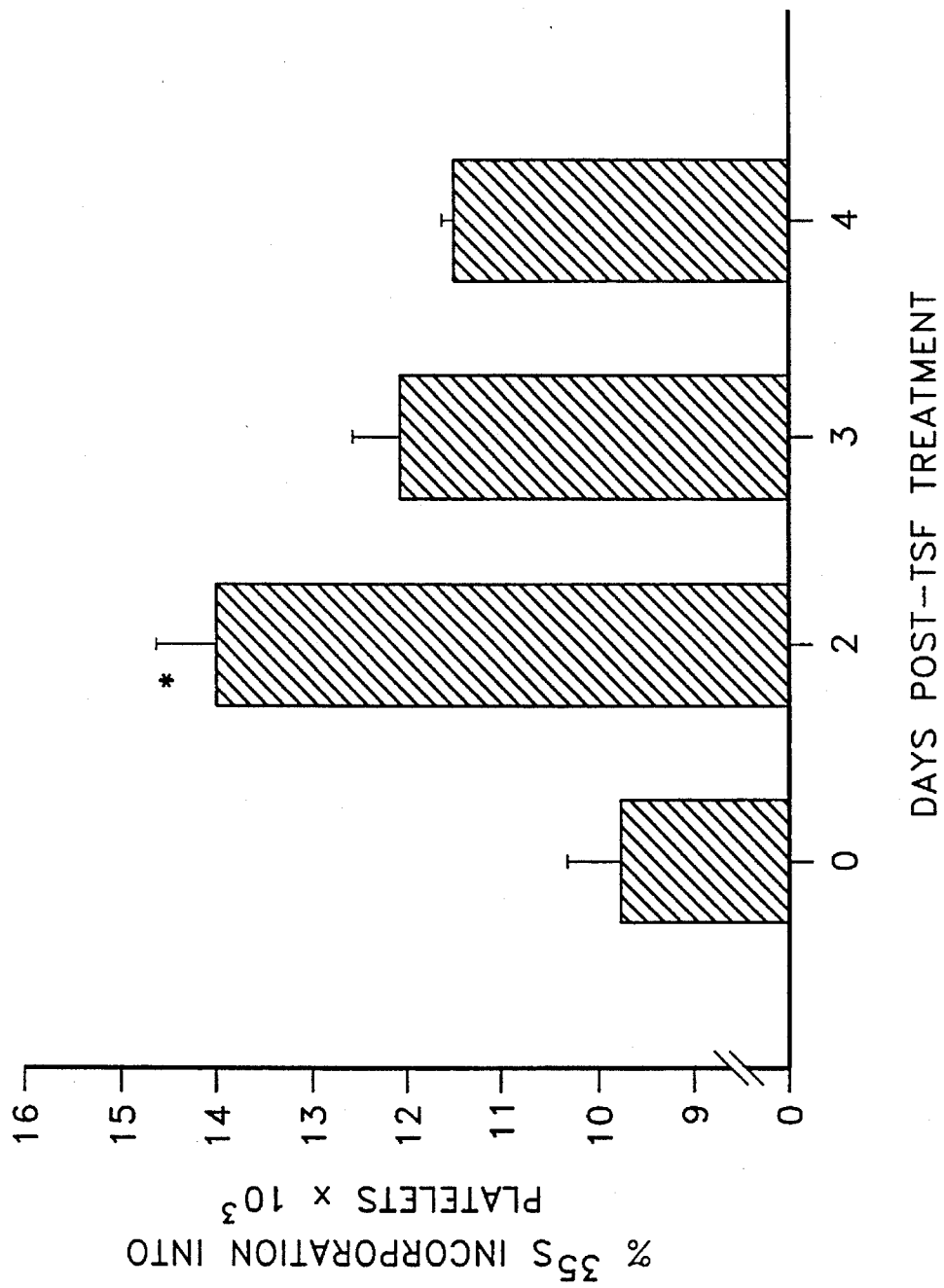
FIG. 6 shows percent $^{35}$S incorporation into platelets of MAIDS mice following treatment with 2 U of TPO. Mice represented on Day 0 were treated on an identical schedule with human serum albumin injections, and sacrificed on the same analysis day as the TSF-treated mice. Data are expressed as mean±S.E. Each bar represented 11–24 mice. * Means were different by Student's $t$ test, p<0.005.
Figure 7:
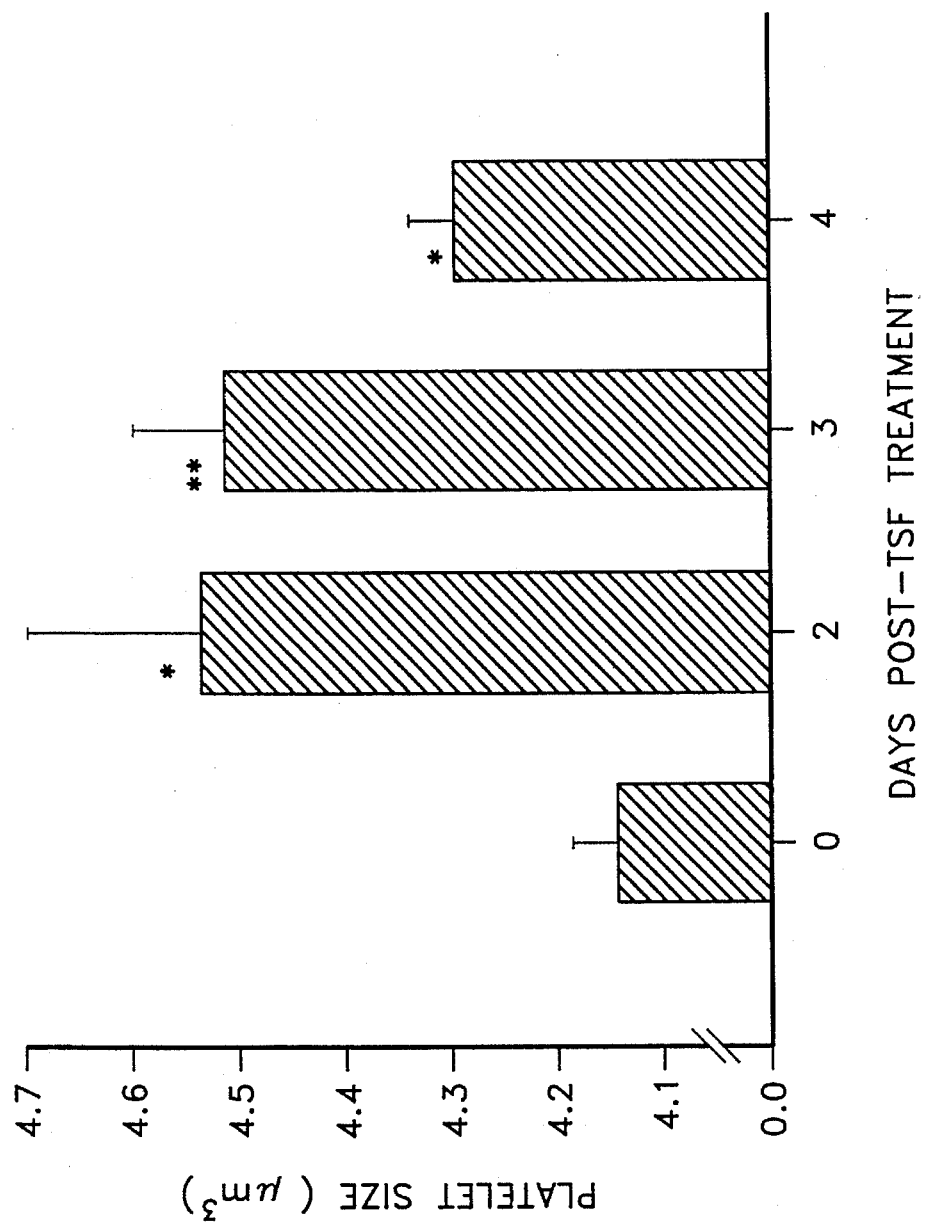
FIG. 7 shows mean platelet size of MAIDS mice following treatment with 2 U of TPO. Mice represented on Day 0 were treated on an identical schedule with human serum albumin injections, and sacrificed on the same analysis day as the TSF-treated mice. Data are expressed as mean±S.E. Each bar represents 10–23 mice. * Means were different by Student's $t$ test, p<0.05, ** p<0.005.
Figure 8:
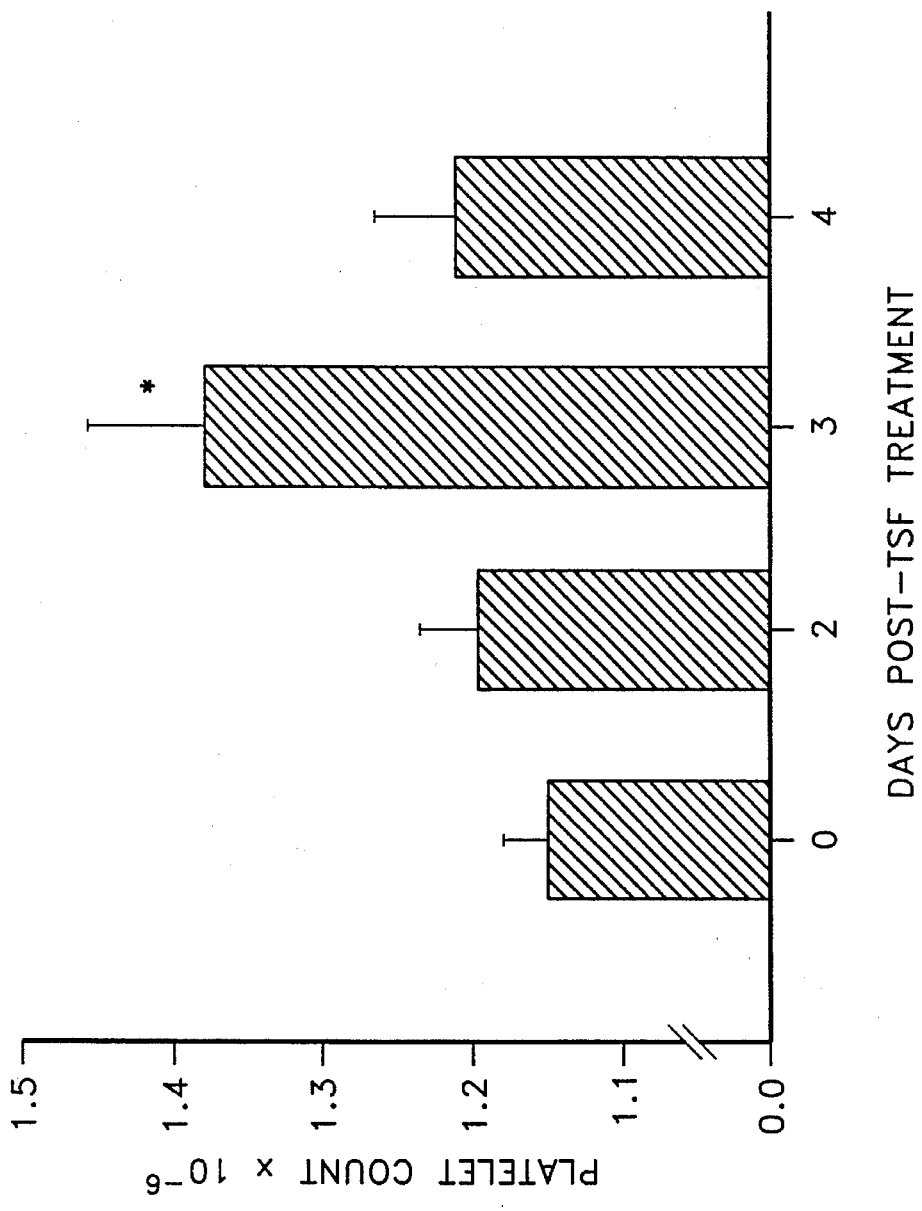
FIG. 8 shows platelet counts of MAIDS mice following treatment with 2 U of TPO. Mice represented on Day 0 were treated on an identical schedule with human serum albumin injections, and sacrificed on the same analysis day as the TPO-treated mice. Data are expressed in mean±S.E. Each bar represents 11–24 mice. * Means were different by Student's $t$ test, p=0.01.

Administration of 2U/mouse of TPO resulted in significantly increased indices of thrombocytopoiesis. Percent $^{35}$S incorporation into platelets was significantly increased above HSA-treated control levels 2 days after TPO treatment (P<0.005, see FIG. 6), and platelet size increased during the same time period (P<0.01, FIG. 7). Both platelet counts (P=0.01, see FIG. 8) and platelet sizes (P<0.005, see FIG. 7) were significantly increased three days after TPO treatment by 121% and 110% of control mice, respectively.

With regards to the above results after treatment with TPO, the following observations may be made. Thrombocytopenia observed in mice following infection with the MuLV (MAIDS model) results primarily from a defect in platelet production, as evidenced by decreased $^{35}$S incorporation into platelets and decreased concentrations of marrow megakaryocytes.

Thrombocytopenia attributable to an immune-mediated mechanism would be expected to result in increased levels of platelet-bound IgG and increased platelet production, neither of which was observed. Circulating platelet lifespan was not measured in the current study, but such a determination would allow further characterization of the mechanism of thrombocytopenia in MuLV infection.

The increased platelet size in MAIDS mice is likely compensatory, as an inverse relationship between platelet count and platelet size has been described. See, Levin, et al, *J Lab Clin Med*, 101:295–307 (1983). Such a compensatory increase would tend to preserve platelet mass ( i.e. platelet count×platelet volume) in the face of thrombocytopenia. Similarly, increased megakaryocyte size may be viewed as compensatory in mice which are exhibiting a concurrent decrease in megakaryocyte number.

The transient thrombocytosis observed at three weeks PI has not been previously reported. Previous efforts have focused primarily on a later time period following MuLV infection. Interestingly, this thrombocytosis coincides temporally with an increased number of naked nuclei in the bone marrow. While not wishing to be bound by any particular theory, one possible explanation which could explain this association is that MuLV infection induces an early shedding of platelets from marrow megakaryocytes. This results in transiently increased platelet counts and concurrent naked nuclei. The finding of naked nuclei in MAIDS mice is strikingly similar to observations in humans with HRT, who have increased numbers of naked nuclei in the bone marrow, even at later stages of infection. This observation provides further evidence of the correlation of MAIDS to thrombocytopenia in HIV/AIDS patients. See, Sloand, *Eur J Hematol*, 48:168–172 (1992); Bauer, et al, *Arch Pathol Lab Med*, 16:1025–1029 (1992). In studies of murine hematopoiesis in which mice were placed in hypoxia, a similar biphasic response in platelet numbers (i.e. initial thrombocytosis followed by eventual thrombocytopenia) was reported to occur, albeit in a shorter timeframe. See, McDonald, *Blood*, 51:165–175 (1978). This phenomenon was attributed to a "stress response", or stress shedding of platelets. Such a mechanism could account for the current observations in MAIDS mice.

Although thrombocytopenic mice would be expected to have higher than usual TPO levels (assuming that the mechanism of thrombocytopenia has not impaired TPO production), it has been previously reported that additional exogenous TPO is beneficial in increasing platelet counts in sublethally irradiated mice. See, Carter and McDonald, *Radiat Res*, 132:74–81 (1992).

Although many patients with HRT have mild decreases in platelet counts and are asymptomatic, specific therapy for thrombocytopenia would be indicated for those patients with platelet counts of less than 50,000/µl as a substantial percentage of those patients are symptomatic. See, Sloand, et al, *Eur J. Hematol*, 48:168–172 (1992).

Based on the present results, MAIDS appears to be a suitable correlative model for those cases of HRT in humans, which are caused primarily by a mechanism of decreased platelet production. Since HRT may be multifactorial even within a single patient, it is apparent that MAIDS is an appropriate model for that portion of thrombocytopenia which is attributable to decreased production of platelets in the individual patient. Also based on these results, MAIDS does not seem an appropriate model for those cases of HRT which are primarily immune-mediated in their pathophysiology (perhaps those cases more commonly observed early in the course of HIV-infection). See, Najean, et al, *J Lab Clin Med*, 123:415–420 (1994). Yet recent indications seem to show that most HIV/AIDS patients suffer from a decrease in platelet production, which is not immune-mediated. It is therefore believed that most of these patients would benefit from TPO administration by way of the present invention.

It is evident that the enclosed data demonstrates that TPO increases platelet counts in MAIDS mice. It is therefore believed that TPO, particularly the C-terminal fragment thereof, is a suitable specific therapy for thrombocytopenic HRT, and generally for other medical conditions which adversely result in low platelet counts.

The importance and relevance of the results in the MAIDS mouse model become even more apparent in view of certain recent theories pertaining to the course of illness in HIV/AIDS patients. This is in view of recent patient data which suggests that if one were able to suppress or prevent the thrombocytopenia that has been observed very early with the onset of HIV infection in a number of HIV patients, one may well advantageously be able to lengthen the time between HIV infection and the onset of full-blown AIDS. While the data (unpublished) is still preliminary, a milder course of thrombocytopenia in HIV-infected patients may correlate well with an advantageous delay in the onset of AIDS symptoms.

By providing a treatment for thrombocytopenia in HIV-infected patients, it is therefore proposed that the compositions and methods of the present invention may unexpectedly and advantageously provide for a significant delay in the onset of AIDS. The advantages of such treatment and delay in the onset of AIDS then are readily apparent.

Thus, the C-terminal fragment of TPO purified to homogeneity from cell sources such as HEK, or produced recombinantly or synthetically, may be used in a pharmaceutical composition or formulation to stimulate platelet recovery in thrombocytopenic patients, including HIV/AIDS and chemotherapy patients. Patients suffering from thrombocytopenias associated with marrow hypoplasia, e.g., aplastic anemia following bone marrow transplantation or adverse side effects of various drugs can also benefit by way of the methods and compositions of the present invention. Other conditions characterized by decreased platelet counts would also benefit by way of the present invention.

Within the scope of the invention is the treatment of disorders resulting from defects in platelets or damage to platelets, e.g., resulting from transient poisoning of platelets by other chemical or pharmaceutical agents or therapeutic manipulations.

Therapeutic treatment of such thrombocytopenic disorders or deficiencies with the compositions of the present invention can avoid undesirable side effects which result from treatment with presently available serum-derived factors or transfusions of human platelets, which may pose serious health risks.

Yet another aspect then of the present invention is therapeutic methods utilizing the compositions of the invention for treating thrombocytopenic disorders. Such compositions comprise a therapeutically effective amount of the C-terminal fragment of TPO in admixture with a pharmaceutically acceptable carrier. A therapeutically-effective amount is that amount which is sufficient to substantially increase platelet counts to within normal or normal parameters.

Based upon the activity profile elicited by the C-terminal fragment of TPO in the above-described scientifically-recognized animal model, this therapeutic amount then is considered to constitute an amount sufficient to increase platelet counts in patients in need thereof by at least about 20% or greater above a baseline count within about 2 to 4 days after TPO administration. In patients with uncompromised marrow, a more suitable amount of platelet increase would be about 100%.

With regards to therapeutic amounts, the dosage regimen for treating the above-described conditions by way of the present invention will be determined by the attending physician giving consideration to various factors, such as, the condition, the body weight, the sex and diet of the patient, the severity of any infection, time of administration and other clinical factors. Generally, the daily regimen should be within a range of about 1 ng to about 10 µg of TPO or about 40 to about 400,000 units of TPO/kg of body weight. TPO may be administered over a period of time sufficient for therapeutically increasing and maintaining platelet cell count numbers. Progress of the treated patient, as measured by an increase in platelet cell counts, can be readily monitored by standard techniques.

With respect to the methods of the present invention, the therapeutic composition can be administered orally or parenterally by means readily known to one of skill in the art for such administrations. Particularly, the composition may be administered intravenously. If desirable, the composition may be also administered subcutaneously. When systemically administered, the therapeutic composition is in the form of a pyrogen-free, parenterally acceptable aqueous solution. The preparation of such pharmaceutically acceptable solutions, having due regard to pH, isotonicity, stability, and the like, is within the skill of the art.

The therapeutic methods and compositions of the present invention may also be employed, alone or in combination, with other cytokines, hematopoietins, interleukins, growth factors, or antibodies in the treatment of disease states characterized by other symptoms of other cellular deficiencies as well as platelet deficiencies. It is anticipated that it will prove useful in treating some forms of thrombocytopenia by administering TPO along with other general stimulators of hematopoiesis, such as erythropoietin (EPO), GM-CSF, G-CSF, IL-3, IL-6 and IL-11. Other megakaryocytic stimulatory factors, e.g., meg-CSF, or other molecules with TPO-like activity may also be employed with TPO. Additional exemplary cytokines or hematopoietins for such co-administration include CSF-1, IL-1, IL-2, IL-4, M-CSF, and IL-7. The dosage recited above for TPO would be adjusted accordingly to compensate for such additional components in the therapeutic composition.

As described in U.S. Pat. No. 5,128,499, TPO was isolated and purified from a human embryonic kidney cell line (HEK). TPO for use in the present invention may also be produced via recombinant techniques. To obtain the DNA sequence for TPO, the purified TPO material is reduced and digested with trypsin. Tryptic fragments are isolated and sequenced by conventional techniques. Oligonucleotide probes are synthesized using the genetic code to. predict all possible sequences that encode the amino acid sequences of the tryptic fragments. Several sequences are generated as probes. The TPO cDNA is identified by using these probes to screen a human genomic library. Alternatively, the mRNA from a cell source of TPO (such as HEK) can be used to make a cDNA library which can be screened with the probes to identify the cDNA encoding the TPO polypeptide.

Using these probes to screen a human genomic library, a cDNA clone is obtained. To obtain a full length clone, the obtained cDNA sequences may be employed as probes to rescreen the library and hybridize to the full length TPO sequence.

The human cDNA for TPO can also be obtained by subcloning a full length human genomic clone into an expression vector, transfecting it into COS cells, preparing a cDNA library from these transfected cells and screening by hybridization for TPO cDNA. Once the entire cDNA is identified, it or any portion of it that encodes an active fragment of TPO, such as the C-terminal fragment, can be introduced into any one of a variety of expression vectors to make an expression system for TPO.

The nucleotide and amino acid sequence of human TPO is shown in FIG. 9.

Methods of producing recombinant TPO are described in de Sauvage et al, *Nature*, 369:533–538 (1994); Lok et al. *Nature*, 369:565–568 (1994); Kaushansky et al, *Nature*, 369:568–571 (1994); Wendling et al.; *Nature*, 369:571–574 (1994), which are incorporated herein by reference.

By such use of recombinant techniques, additional DNA sequences also encoding the TPO polypeptide may be obtained. The present invention also encompasses these DNA sequences, free of association with DNA sequences encoding other proteins, and coding on expression for TPO polypeptides. These DNA-sequences include those sequences which hybridize under stringent hybridization conditions. See, T. Maniatis et al, *Molecular Cloning (A Laboratory Manual)*. Cold Spring Harbor Laboratory (1982), pages 387 to 389 to the DNA sequences.

An example of one such stringent hybridization condition is hybridization in 4XSSC at 65° C. for an hour. Alternatively an exemplary stringent hybridization condition is 50% formamide, 4XSSC at 42° C.

DNA sequences which hybridize to the sequences for TPO under relaxed hybridization conditions and which code on expression for TPO peptides having TPO biological properties also encode TPO polypeptides. Examples of such non-stringent hybridization conditions are 4XSSC at 50° C. or hybridization with 30–40% formamide at 42° C. For example, a DNA sequence which shares regions of significant homology, e.g., sites of glycosylation or disulfide linkages, with the sequences of TPO, and encodes a protein having one or more TPO biological properties clearly encodes a TPO polypeptide. This is so even if such a DNA sequence would not stringently hybridize to the TPO sequences.

Allelic variations (naturally-occurring base changes in the species population which may or may not result in an amino acid change) of DNA sequences encoding the peptide sequences of TPO are also included in the present invention, as well as analogs or derivatives thereof. Similarly, DNA sequences which code for TPO polypeptides but which differ in codon sequence due to the degeneracies of the genetic code or variations in the DNA sequence of TPO which are caused by point mutations or by induced modifications to enhance the activity, half-life or production of TPO encoded thereby are also encompassed in the invention.

Modifications in the peptides or DNA sequences encoding TPO can be made by one skilled in the art using known techniques. Modifications of interest in the TPO sequences may include the replacement, insertion, or deletion of a selected amino acid residue in the coding sequences. These modifications also encompass substitutions at the 5' and 3' ends of the DNA sequence of FIG. 9. Mutagenic techniques for such replacement, insertion, or deletion are well known to one skilled in the art. See, e.g., U.S. Pat. No. 4,518,584, which is incorporated herein by reference.

Specific mutations of the sequences of the TPO polypeptide may involve modifications of a glycosylation site. The absence of glycosylation or only partial glycosylation results from amino acid substitution or deletion at any asparagine-linked glycosylation recognition site or at any site on the molecule that is modified by addition of O-linked carbohydrate. An asparagine-linked glycosylation recognition site comprises a tripeptide sequence which is specifically recognized by appropriate cellular glycosylation enzymes. These tripeptide sequences are either Asp-X-Thr or Asp-X-Ser, where X can be any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

Other analogs and derivatives of the sequence of TPO which would be expected to retain TPO activity in whole or in part may also be easily made by one of skill in the art given the disclosures herein. One such modification may be the attachment of polyethylene glycol (PEG) onto existing lysine residues in the TPO sequence. Another modification is the insertion of one or more lysine residues or other amino acid residues into the sequence that can react with PEG or PEG derivatives by conventional techniques to enable the attachment of PEG moieties. Such modifications are considered to be encompassed by the present invention.

TPO may also be produced by known conventional chemical synthesis. Methods for constructing TPO synthetically are known to those of skill in the art. The synthetically-constructed TPO polypeptide sequences, by virtue of sharing primary, secondary, or tertiary structural and conformational characteristics with TPO, may thus also possess biological properties in common therewith. Thus, they may be employed as biologically active substitutes for natural, purified TPO or recombinant TPO in the therapeutic methods of the present invention.

The present invention also provides a method for expressing recombinant TPO. One method of the present invention involves introducing the cDNA encoding TPO into an expression vector to make an expression system for TPO. A selected host cell is transformed with the vector and cultured. The method of the present invention therefore comprises culturing a suitable cell or cell line, which has been transformed with a DNA sequence coding on expression for TPO under the control of known regulatory sequences. Regulatory sequences include promoter sequences, terminator sequences and other suitable sequences which direct the expression of the protein in an appropriate host cell. The expressed TPO is then recovered, isolated and purified from the culture medium (or from the cell, if expressed intracellularly) by appropriate means known to one of skill in the art.

Suitable cells or cell lines may be mammalian cells, such as Chinese hamster ovary cells (CHO) or 3T3 cells. The selection of suitable mammalian host cells and methods for transformation, culture, amplification, screening, and product production and purification are known in the art. See, e.g., Gething and Sambrook, *Nature*, 293:620–625 (1981), or alternatively, Kaufman et al, *Mol. Cell. Biol.*, 5 (7):1750–1759 (1985) or Howley et al, U.S. Pat. No. 4,419, 446. Other suitable mammalian cell lines are the monkey COS-1 cell line, and the CV-1 cell line. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells may be genotypically deficient in the selection gene. Other suitable mammalian cell lines include; but are not limited to, HeLa, mouse L-929, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art are also available as host cells for expression of TPO. Additionally, where desired, insect cells may be utilized as host cells in the method of the present invention. See e.g., Miller et al, *Genetic Engineering*, 8:277–298 (Plenum Press 1986) and references cited therein.

The present invention also provides recombinant molecules or vectors for use in the method of expression of TPO. The vectors contain the TPO DNA sequences, which alone or in combination with other sequences, code for TPO. Alternatively, vectors incorporating modified sequences as described above are also embodiments of the present invention and useful in the production of TPO. The vectors employed in the method also contain selected regulatory sequences in operative association with the DNA coding sequences of the invention, and are capable of directing the replication and expression thereof in selected host cells.

One vector is pXM, which is particularly desirable for expression in COS cells. See, Y. C. Yang et al, *Cell*, 47:3–10 (1986). Another vector which is desirable for expression in mammalian cells, e.g., CHO cells, is pEMC2B1. Mammalian cell expression vectors described herein may be synthesized by techniques well known to those skilled in this art. The components of the vectors, e.g., replicons, selection genes, enhancers, promoters, and the like, may be obtained from natural sources or synthesized by known procedures.

See, Kaufman et al, *J. Mol. Biol.* 159:511–521 (1982); and Kaufman, *Proc. Natl. Acad. Sci., USA,* 82:689–693 (1985). Alternatively, the vector DNA may include all or part of the bovine papilloma virus genome (Lusky et al, *Cell,* 36:391–401 (1984)) and be carried in cell lines such as C127 mouse cells as a stable episomal element. The transformation of these vectors into appropriate host cells can result in expression of TPO.

Other appropriate expression vectors of which numerous types are known in the art for mammalian, insect, yeast, fungal and bacterial expression can also be used for this purpose.

The following examples are for illustration and should not be construed as limiting the scope of the present invention.

EXAMPLES

Example 1

Animals and Virus

Male C57BL/6 mice were obtained from Harlan Sprague Dawley (Indianapolis, IN). All mice were 4–5 weeks of age at the time of the MuLV infection.

Murine leukemia viruses (ecotropic and mink-cell focus forming, or MCF) were obtained from Ogden Bioservices Corporation (Rockville, Md.). Direct pelleted viruses were resuspended in Dulbecco's medium to a final concentration of $10^5$ each of the ecotropic and MCF infectious or colony forming units per ml of medium. Dulbecco's medium with no virus was used as a control substance. Mice were injected with 0.5 ml of the virus suspension or of the control medium by a single intraperitoneal injection.

Example 2

Thrombopoietin

A partially purified Step II TPO obtained from human embryonic kidney (HEK) cell cultures was used as described in U.S. Pat. No. 5,128,499. The specific activity of the TPO was 3.93 units (U)/mg protein (2.55 mg protein/ml). The protein in this preparation was principally human serum albumin (HSA), which was added to the TPO preparation to stabilize the hormone. HSA, (Sigma Chemical Co., St. Louis, Mo.) the carrier protein, was prepared to a final concentration of 2.55 mg/ml and was used as a negative control. A unit of TPO was previously defined as the amount of material (expressed in mg of protein) needed to increase percent $^{35}S$ incorporation into platelets of immunothrombocythemic mice to 50% above control levels.

No detectable levels of interleukin (IL)1 alphal , IL-1 beta, or tumor necrosis factor (TNF) were found in this TPO preparation. Furthermore, Step II TPO was tested for the presence of IL-6 and endotoxin. Utilizing ELISA assay, <0.25 µg or <2500 U of IL-6 (below the sensitivity of the assay) per U of TPO was present; also, <2.5 U of endotoxin per U of TPO were detected by the E-toxate Limulus Amebocyte Lysate test (Sigma Chemical Company, St. Louis, Mo.). I have previously provided evidence that >40,000 U of Il-6 administered over a 2-day period or >50U of endotoxin were needed to stimulate platelet production in mice. See, McDonald, et al, *Blood,* 77:735–740 (1991).

Example 3

Experimental Design

Mice were injected with MuLV on day 0, and were subsequently sacrificed 3–9 weeks post infection (PI) with no further treatment. Other mice were virus infected and treated with TPO (2 U/mouse, divided into four equal doses and administered by subcutaneous injection twice daily for 2 days), and sacrificed 2,3 or 4 days later at 9 weeks PI.

At the time of the sacrifice, hematocrits, platelet counts, reticulocyte counts and RBC and WBC counts were determined from blood taken from the retroorbital sinus. Five minutes after an i.p. injection of a heparin-sodium pentobarbital solution, 0.5 ml of blood was collected via cardiac puncture into syringes containing 1.0 ml of 3.8% sodium citrate solution. See, McDonald, *Proc Soc Exp Biol Med,* 144:1006–1012 (1973). This blood was used for determination of percent $^{35}S$ incorporation into platelets, platelet volumes, and platelet-bound IgG. Also, one femur was removed for measurement of megakaryocyte size and number. Hematocrits were measured by a standard microtechnique and platelet counts were obtained manually by use of phase contrast microscopy.

Example 4

Platelet Volume Measurements

For platelet sizing, platelet-rich plasma (PRP) was obtained by centrifugation of whole blood at 160 g for 4.5 min. at 22° C. Platelet sizing was performed using an Electrozone/Celloscope (Particle Data Inc., Elmhurst, Ill.) with a logarithmic scale as previously described. See, McDonald, *Br J Hematol,* 34:257–267 (1976). The instrument was set at log 10, current 6 and gain 4. Calibration was monitored frequently by using 2.02 µm diameter latex particles to standardize the instrument. A 48 µm orifice was used for all size determinations.

Example 5

Percent $^{35}S$ incorporation into platelets

Percent $^{35}S$ incorporation into platelets was determined 24 hours after an i.p. injection of 30 µCi of $^{35}S$ in 0.5 ml saline. The PRP not used for platelet sizing measurements was resuspended with the blood, and 1 ml of 1% EDTA in 0.538% NaCl was then added. To obtain the PRP, blood was centrifuged at 450 g for 4.5 min. at 4° C. to obtain a platelet button. The platelets from each mouse were resuspended in 0.6 ml of 1% ammonium oxalate, mixed, centrifuged (15 min at 800 g), and washed one additional time with 0.5 ml of 1% ammonium oxalate. A final wash in 1.5 ml of saline was made prior to counting platelet suspensions on the Celloscope and measuring radioactivity of the platelets. The percent $^{35}S$ incorporation into platelets was calculated as previously described. See, McDonald, *Proc Soc Exp Biol Med,* 144:1006–1012 (1973).

Example 6

Megakaryocyte Size and Number

To determine the size and number of megakaryocytes in the marrow of MuLV-infected mice, the femurs removed at the time of sacrifice were fixed in 10% formalin, and histological sections were prepared as previously described. See, Cullen, et al, *Exp Hematol,* 14:782–788 (1986). The sections were processed for light microscopy by embedding in glycol methacrylate, followed by staining with hematoxylin and eosin.

Megakaryocyte size was determined by randomly selecting sections of each femur and counting 200 megakaryocyte profiles using section profile perimeter measurements. Corrections for tissue shrinkage, section thickness, and optically lost profiles were made prior to statistical analysis of mean diameters and mean megakaryocyte numbers. See, Cullen, et al, *Exp Hematol*, 14:782–788 (1986). The number of megakaryocytes was obtained from marrow sections at 400×magnification and is expressed as cells per mm$^3$ of marrow.

Example 7

Determination of platelet-bound immunoglobulin

For measurement of platelet-bound immunoglobulin G (IgG), a sample of platelet suspension remaining after washing as described above was utilized. The average concentration of platelets was 7.7×10$^7$/μl. The cells were then incubated with a saturating concentration (total 5 μl/sample) of a rabbit antimouse IgG–antibody labeled with fluorescein (TAGO, Burlingame, Calif.) for 20 min at 4° C. Each sample was then washed two times with 1.0 ml/wash of standard azide buffer, pH 7.2 (SAB). Cell suspensions were pelleted between washes by centrifugation for 5 mins at 160×g in a 4° C. centrifuge. The FITC labeled cells were then resuspended in 100 μl of SAB, and while vortexing, 100 μl of 2% paraformaldehyde solution was added. The platelets were analyzed on an FACSCAN Flow Cytofluorometer (Becton-Dickinson, Immunocytochemistry Systems, Braintree, Mass.). Ten thousand platelets were examined for each sample; the mean fluorescence per platelet was calculated from the acquired data. In each experiment, a non-specific antibody (goat-anti-rabbit IgG, Chemicon, Temecula, Calif.) was used as a negative control. Statistical analysis of the data was performed using the PROC GLM and PROC TTEST procedure in SAS.

Example 8

Naked Nuclei

For each mouse, the number of naked megakaryocyte nuclei was determined by averaging the numbers of naked nuclei in 8–12 fields at 1000×magnification.

In view of the above, this invention provides improved therapies for low platelet count in patients experiencing thrombocytopenia.

At present, AZT is the treatment of choice for thrombocytopenia associated with AIDS, but such treatment has many known undesirable side effects. TPO utilized by the methods and compositions of the present invention has fewer toxic effects than AZT. Additionally, it is believed that TPO utilized by way of the present invention is a specific and efficacious treatment for medical conditions which are characterized by poor or deficient platelet production, including HIV/AIDS and chemotherapy, among others. It is therefore contemplated that the present invention provides a safer and more effective treatment for thrombocytopenia than has been previously achieved.

Although various embodiments of this invention have been illustrated, this was for the purpose of describing, and not limiting the invention. Various modifications, which will become apparent to one skilled in the art, are within the scope of this invention.

What I claim is:

1. A method of increasing platelet cell counts in a patient in need thereof which comprises administering to the patient a therapeutic composition comprising a therapeutic amount of a C-terminal fragment of thrombopoietin and a pharmaceutically acceptable carrier, said therapeutic amount being sufficient to increase platelet cell counts in said patient by at least about 20% above a baseline count within about 2 to 4 days after C-terminal fragment administration.

2. The method of claim 1 wherein the patient has undergone chemotherapy or radiation.

3. The method of claim 1 wherein the patient is immunodeficient.

4. The method of claim 3, wherein the patient has HIV/AIDS.

5. The method of claim 1 wherein the therapeutic amount of the C-terminal fragment administered ranges from about 40 to about 400,000 units per kg of body weight per day.

6. The method of claim 5 wherein the C-terminal fragment is administered for a time sufficient to therapeutically increase and maintain platelet cell counts.

7. The method of claim 1, wherein the composition further comprises a cytokine selected from the group consisting of erythropoietin (EPO), granulocyte-colony-stimulating factor (G-CSF), colony-stimulating factor (CSF-1), granulocyte-macrophage colony-stimulating factor (GM-CSF), interleukin-1 (IL-1), interleukin-3 (IL-3), interleukin-4 (IL-4), interleukin-6 (IL-6), interleukin-7(IL-7), interlukin-11 (IL-11), megakaryocyte-stem cell factor (meg-SCF), and megakaryocyte-colony-stimulating factor (M-CSF).

8. The method of claim 7 wherein the cytokine is EPO, GM-CSF, or G-CSF.

9. A method of increasing platelet cell counts in vivo in a patient experiencing thrombocytopenia which comprises administering to said patient at least about 40 units of a c-Mpl receptor binding ligand per kg of body weight and a pharmaceutically acceptable carrier.

10. The method of claim 9, wherein the patient has HIV/AIDS.

11. The method of claim 9, wherein the patient has undergone chemotherapy or radiation treatment.

12. The method of claim 9, wherein the ligand has a specific activity of at least about 4 units/mg of protein.

13. A method of treating thrombocytopenia in vivo, comprising:

(a) providing a C-terminal fragment of an active TPO polypeptide characterized by having a molecular weight as determined by sodium dodecyl sulfate-polyacrylamide gel electrophoresis of about 15,000 daltons as a monomer, and about 30,000 daltons as a dimer, a specific activity of at least about 21,000 units/mg, wherein a unit of specific activity is determined by dividing one milligram by the weight of the active TPO polypeptide required to increase the percent $^{35}S$ incorporation into platelets of mice by 50 percent above a control baseline in an immunothrombocythemic assay, and being capable of being stained by Coomassie blue;

(b) combining said C-terminal fragment with a pharmaceutically acceptable carrier; and (c) administering said C-terminal fragment and said carrier to a patient to increase and maintain platelet cell counts by at least about 20% above a baseline count.

14. A therapeutic composition for administering to a patient to increase platelet cell counts, which composition comprises a therapeutic amount of a C-terminal fragment of thrombopoietin and a pharmaceutically acceptable carrier, said therapeutic amount being sufficient to increase platelet cell counts in said patient by at least about 20% above a baseline count within about 2 to 4 days after C-terminal fragment administration.

15. The therapeutic composition of claim 14 wherein the therapeutic amount ranges from about 40 to about 400,000 units per kg of body weight.

16. The therapeutic composition of claim 14, wherein the composition further comprises a cytokine selected from the group consisting of erythropoietin (EPO), granulocyte-colony-stimulating factor (G-CSF), colony-stimulating factor (CSF-1), granulocyte-macrophage colony-stimulating factor (GM-CSF), interleukin-1 (IL-1), interleukin-3 (IL-3), interleukin-4 (IL-4), interluekin-6 (IL-6), interleukin-7 (IL-7), interleukin-11 (IL-11), megakaryocyte-stem cell factor (meg-SCF), and megakaryocyte-colony-stimulating factor (M-CSF).

17. The therapeutic composition of claim 16 wherein the cytokine is EPO, GM-CSF, or G-CSF.

18. A composition for increasing platelet cell counts in vivo in a patient experiencing thrombocytopenia, which composition comprises at least about 40 units of a c-Mpl receptor binding ligand per kg of body weight and a pharmaceutically acceptable carrier.

19. A therapeutic composition for treating thrombocytopenia in vivo, which composition comprises a C-terminal fragment of an active TPO polypeptide characterized by having a molecular weight as determined by sodium dodecyl sulfate-polyacrylamide gel electrophoresis of about 15,000 daltons as a monomer, and about 30,000 daltons as a dimer, a specific activity of at least about 21,000 units/mg, wherein a unit of specific activity is determined by dividing one milligram by the weight of the active TPO polypeptide required to increase the percent $^{35}$S incorporation into platelets of mice by 50 percent above a control baseline in an immunothrombocythemic mouse assay, and being capable of being stained by Coomassie blue, and a pharmaceutically acceptable carrier said C-terminal fragment present in an amount to increase platelet cell counts by at least about 20% above a baseline count.

20. A method of increasing platelet cell counts in a patient in need thereof which comprises administering to the patient a therapeutic composition comprising a therapeutic amount of thrombopoietin or an active fragment of thrombopoietin and a pharmaceutically acceptable carrier, said therapeutic amount being sufficient to increase platelet cell counts in said patient by at least about 20% above a baseline count.

21. The method of claim 20, wherein the patient has HIV/AIDS.

22. The method of claim 20 wherein the active fragment is selected from the group consisting of the N-terminal and C-terminal fragments.

23. The method of claim 22 wherein the active fragment is the N-terminal fragment.

24. The method of claim 22 wherein the active fragment is the C-terminal fragment.

25. The method of claim 20, wherein the patient has undergone chemotherapy or radiation treatment.

26. The method of claim 25, wherein the therapeutic amount administered ranges from about 40 to about 400,000 units/kg of body weight per day.

27. The method of claim 26, wherein the thrombopoietin or active fragment has a specific activity of at least about 4 units/mg of protein.

* * * * *

Adverse Decision in Interference

Patent No. 5,593,666, Ted P. McDonald, METHODS AND COMPOSITIONS FOR TREATING THROMBOCYTOPENIA, Interference No. 104,544, final judgment adverse to the patentees rendered May 17, 2004, as to claims 1-27.

(*Official Gazette November 27, 2007*)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1795 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 216..1274

( i x ) FEATURE:
        ( A ) NAME/KEY: mat_peptide
        ( B ) LOCATION: 279..1274

( x i ) SEQUENCE DESCRIPTION: SEQ ID NO:1:

```
TCTTCCTACC  CATCTGCTCC  CCAGAGGGCT  GCCTGCTGTG  CACTTGGGTC  CTGGAGCCCT         60

TCTCCACCCG  GATAGATTCC  TCACCCTTGG  CCCGCCTTTG  CCCCACCCTA  CTCTGCCCAG        120

AAGTGCAAGA  GCCTAAGCCG  CCTCCATGGC  CCAGGAAGG   ATTCAGGGGA  GAGGCCCCAA        180

ACAGGGAGCC  ACGCCAGCCA  GACACCCCGG  CCAGA  ATG  GAG  CTG  ACT  GAA  TTG        233
                                          Met  Glu  Leu  Thr  Glu  Leu
                                          -21                       -20

CTC  CTC  GTG  GTC  ATG  CTT  CTC  CTA  ACT  GCA  AGG  CTA  ACG  CTG  TCC  AGC    281
Leu  Leu  Val  Val  Met  Leu  Leu  Leu  Thr  Ala  Arg  Leu  Thr  Leu  Ser  Ser
```

-continued

| | -15 | | | | | -10 | | | | | -5 | | | | | 1 | |
|---|---|---|---|---|---|---|---|---|---|---|---|---|---|---|---|---|---|
| CCG | GCT | CCT | CCT | GCT | TGT | GAC | CTC | CGA | GTC | CTC | AGT | AAA | CTG | CTT | CGT | | 329 |
| Pro | Ala | Pro | Pro | Ala | Cys | Asp | Leu | Arg | Val | Leu | Ser | Lys | Leu | Leu | Arg | | |
| | | | 5 | | | | | 10 | | | | | 15 | | | | |
| GAC | TCC | CAT | GTC | CTT | CAC | AGC | AGA | CTG | AGC | CAG | TGC | CCA | GAG | GTT | CAC | | 377 |
| Asp | Ser | His | Val | Leu | His | Ser | Arg | Leu | Ser | Gln | Cys | Pro | Glu | Val | His | | |
| | | 20 | | | | | 25 | | | | | 30 | | | | | |
| CCT | TTG | CCT | ACA | CCT | GTC | CTG | CTG | CCT | GCT | GTG | GAC | TTT | AGC | TTG | GGA | | 425 |
| Pro | Leu | Pro | Thr | Pro | Val | Leu | Leu | Pro | Ala | Val | Asp | Phe | Ser | Leu | Gly | | |
| | | 35 | | | | | 40 | | | | | 45 | | | | | |
| GAA | TGG | AAA | ACC | CAG | ATG | GAG | GAG | ACC | AAG | GCA | CAG | GAC | ATT | CTG | GGA | | 473 |
| Glu | Trp | Lys | Thr | Gln | Met | Glu | Glu | Thr | Lys | Ala | Gln | Asp | Ile | Leu | Gly | | |
| 50 | | | | | 55 | | | | | 60 | | | | | 65 | | |
| GCA | GTG | ACC | CTT | CTG | CTG | GAG | GGA | GTG | ATG | GCA | GCA | CGG | GGA | CAA | CTG | | 521 |
| Ala | Val | Thr | Leu | Leu | Leu | Glu | Gly | Val | Met | Ala | Ala | Arg | Gly | Gln | Leu | | |
| | | | | 70 | | | | | 75 | | | | | 80 | | | |
| GGA | CCC | ACT | TGC | CTC | TCA | TCC | CTC | CTG | GGG | CAG | CTT | TCT | GGA | CAG | GTC | | 569 |
| Gly | Pro | Thr | Cys | Leu | Ser | Ser | Leu | Leu | Gly | Gln | Leu | Ser | Gly | Gln | Val | | |
| | | | 85 | | | | | 90 | | | | | 95 | | | | |
| CGT | CTC | CTC | CTT | GGG | GCC | CTG | CAG | AGC | CTC | CTT | GGA | ACC | CAG | CTT | CCT | | 617 |
| Arg | Leu | Leu | Leu | Gly | Ala | Leu | Gln | Ser | Leu | Leu | Gly | Thr | Gln | Leu | Pro | | |
| | | 100 | | | | | 105 | | | | | 110 | | | | | |
| CCA | CAG | GGC | AGG | ACC | ACA | GCT | CAC | AAG | GAT | CCC | AAT | GCC | ATC | TTC | CTG | | 665 |
| Pro | Gln | Gly | Arg | Thr | Thr | Ala | His | Lys | Asp | Pro | Asn | Ala | Ile | Phe | Leu | | |
| | 115 | | | | | 120 | | | | | 125 | | | | | | |
| AGC | TTC | CAA | CAC | CTG | CTC | CGA | GGA | AAG | GTG | CGT | TTC | CTG | ATG | CTT | GTA | | 713 |
| Ser | Phe | Gln | His | Leu | Leu | Arg | Gly | Lys | Val | Arg | Phe | Leu | Met | Leu | Val | | |
| 130 | | | | | 135 | | | | | 140 | | | | | 145 | | |
| GGA | GGG | TCC | ACC | CTC | TGC | GTC | AGG | CGG | GCC | CCA | CCC | ACC | ACA | GCT | GTC | | 761 |
| Gly | Gly | Ser | Thr | Leu | Cys | Val | Arg | Arg | Ala | Pro | Pro | Thr | Thr | Ala | Val | | |
| | | | | 150 | | | | | 155 | | | | | 160 | | | |
| CCC | AGC | AGA | ACC | TCT | CTA | GTC | CTC | ACA | CTG | AAC | GAG | CTC | CCA | AAC | AGG | | 809 |
| Pro | Ser | Arg | Thr | Ser | Leu | Val | Leu | Thr | Leu | Asn | Glu | Leu | Pro | Asn | Arg | | |
| | | | 165 | | | | | 170 | | | | | 175 | | | | |
| ACT | TCT | GGA | TTG | TTG | GAG | ACA | AAC | TTC | ACT | GCC | TCA | GCC | AGA | ACT | ACT | | 857 |
| Thr | Ser | Gly | Leu | Leu | Glu | Thr | Asn | Phe | Thr | Ala | Ser | Ala | Arg | Thr | Thr | | |
| | | 180 | | | | | 185 | | | | | 190 | | | | | |
| GGC | TCT | GGG | CTT | CTG | AAG | TGG | CAG | CAG | GGA | TTC | AGA | GCC | AAG | ATT | CCT | | 905 |
| Gly | Ser | Gly | Leu | Leu | Lys | Trp | Gln | Gln | Gly | Phe | Arg | Ala | Lys | Ile | Pro | | |
| | 195 | | | | | 200 | | | | | 205 | | | | | | |
| GGT | CTG | CTG | AAC | CAA | ACC | TCC | AGG | TCC | CTG | GAC | CAA | ATC | CCC | GGA | TAC | | 953 |
| Gly | Leu | Leu | Asn | Gln | Thr | Ser | Arg | Ser | Leu | Asp | Gln | Ile | Pro | Gly | Tyr | | |
| 210 | | | | | 215 | | | | | 220 | | | | | 225 | | |
| CTG | AAC | AGG | ATA | CAC | GAA | CTC | TTG | AAT | GGA | ACT | CGT | GGA | CTC | TTT | CCT | | 1001 |
| Leu | Asn | Arg | Ile | His | Glu | Leu | Leu | Asn | Gly | Thr | Arg | Gly | Leu | Phe | Pro | | |
| | | | | 230 | | | | | 235 | | | | | 240 | | | |
| GGA | CCC | TCA | CGC | AGG | ACC | CTA | GGA | GCC | CCG | GAC | ATT | TCC | TCA | GGA | ACA | | 1049 |
| Gly | Pro | Ser | Arg | Arg | Thr | Leu | Gly | Ala | Pro | Asp | Ile | Ser | Ser | Gly | Thr | | |
| | | | 245 | | | | | 250 | | | | | 255 | | | | |
| TCA | GAC | ACA | GGC | TCC | CTG | CCA | CCC | AAC | CTC | CAG | CCT | GGA | TAT | TCT | CCT | | 1097 |
| Ser | Asp | Thr | Gly | Ser | Leu | Pro | Pro | Asn | Leu | Gln | Pro | Gly | Tyr | Ser | Pro | | |
| | | 260 | | | | | 265 | | | | | 270 | | | | | |
| TCC | CCA | ACC | CAT | CCT | CCT | ACT | GGA | CAG | TAT | ACG | CTC | TTC | CCT | CTT | CCA | | 1145 |
| Ser | Pro | Thr | His | Pro | Pro | Thr | Gly | Gln | Tyr | Thr | Leu | Phe | Pro | Leu | Pro | | |
| | 275 | | | | | 280 | | | | | 285 | | | | | | |
| CCC | ACC | TTG | CCC | ACC | CCT | GTG | GTC | CAG | CTC | CAC | CCC | CTG | CTT | CCT | GAC | | 1193 |
| Pro | Thr | Leu | Pro | Thr | Pro | Val | Val | Gln | Leu | His | Pro | Leu | Leu | Pro | Asp | | |
| 290 | | | | | 295 | | | | | 300 | | | | | 305 | | |
| CCT | TCT | GCT | CCA | ACG | CCC | ACC | CCT | ACC | AGC | CCT | CTT | CTA | AAC | ACA | TCC | | 1241 |
| Pro | Ser | Ala | Pro | Thr | Pro | Thr | Pro | Thr | Ser | Pro | Leu | Leu | Asn | Thr | Ser | | |

|   |   |   |   | 310 |   |   |   | 315 |   |   |   | 320 |   |   |      |
|---|---|---|---|---|---|---|---|---|---|---|---|---|---|---|------|
| TAC | ACC | CAC | TCC | CAG | AAT | CTG | TCT | CAG | GAA | GGG | TAAGGTTCTC | AGACACTGCC |   |   | 1294 |
| Tyr | Thr | His | Ser | Gln | Asn | Leu | Ser | Gln | Glu | Gly |   |   |   |   |      |
|   |   |   | 325 |   |   |   |   | 330 |   |   |   |   |   |   |      |

| GACATCAGCA | TTGTCTCATG | TACAGCTCCC | TTCCCTGCAG | GGCGCCCCTG | GGAGACAACT | 1354 |
| GGACAAGATT | TCCTACTTTC | TCCTGAAACC | CAAAGCCCTG | GTAAAAGGGA | TACACAGGAC | 1414 |
| TGAAAAGGGA | ATCATTTTTC | ACTGTACATT | ATAAACCTTC | AGAAGCTATT | TTTTAAGCT | 1474 |
| ATCAGCAATA | CTCATCAGAG | CAGCTAGCTC | TTTGGTCTAT | TTTCTGCAGA | AATTTGCAAC | 1534 |
| TCACTGATTC | TCTACATGCT | CTTTTTCTGT | GATAACTCTG | CAAAGGCCTG | GGCTGGCCTG | 1594 |
| GCAGTTGAAC | AGAGGGAGAG | ACTAACCTTG | AGTCAGAAAA | CAGAGAAAGG | GTAATTTCCT | 1654 |
| TTGCTTCAAA | TTCAAGGCCT | TCCAACGCCC | CCATCCCCTT | TACTATCATT | CTCAGTGGGA | 1714 |
| CTCTGATCCC | ATATTCTTAA | CAGATCTTTA | CTCTTGAGAA | ATGAATAAGC | TTTCTCTCAG | 1774 |
| AAAAAAAAAA | AAAAAAAAA | A |   |   |   | 1795 |

( 2 ) INFORMATION FOR SEQ ID NO:2:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Leu | Thr | Glu | Leu | Leu | Leu | Val | Val | Met | Leu | Leu | Leu | Thr | Ala |
| -21 | -20 |   |   |   | -15 |   |   |   |   | -10 |   |   |   |   |   |

| Arg | Leu | Thr | Leu | Ser | Ser | Pro | Ala | Pro | Pro | Ala | Cys | Asp | Leu | Arg | Val |
| -5  |   |   |   |   | 1 |   |   |   | 5 |   |   |   |   |   | 10 |

| Leu | Ser | Lys | Leu | Leu | Arg | Asp | Ser | His | Val | Leu | His | Ser | Arg | Leu | Ser |
|   |   |   | 15 |   |   |   |   | 20 |   |   |   |   | 25 |   |   |

| Gln | Cys | Pro | Glu | Val | His | Pro | Leu | Pro | Thr | Pro | Val | Leu | Leu | Pro | Ala |
|   |   | 30 |   |   |   |   | 35 |   |   |   |   | 40 |   |   |   |

| Val | Asp | Phe | Ser | Leu | Gly | Glu | Trp | Lys | Thr | Gln | Met | Glu | Glu | Thr | Lys |
|   | 45 |   |   |   |   | 50 |   |   |   |   | 55 |   |   |   |   |

| Ala | Gln | Asp | Ile | Leu | Gly | Ala | Val | Thr | Leu | Leu | Leu | Glu | Gly | Val | Met |
| 60 |   |   |   |   | 65 |   |   |   |   | 70 |   |   |   |   | 75 |

| Ala | Ala | Arg | Gly | Gln | Leu | Gly | Pro | Thr | Cys | Leu | Ser | Ser | Leu | Leu | Gly |
|   |   |   |   | 80 |   |   |   |   | 85 |   |   |   |   | 90 |   |

| Gln | Leu | Ser | Gly | Gln | Val | Arg | Leu | Leu | Leu | Gly | Ala | Leu | Gln | Ser | Leu |
|   |   |   | 95 |   |   |   |   | 100 |   |   |   |   | 105 |   |   |

| Leu | Gly | Thr | Gln | Leu | Pro | Pro | Gln | Gly | Arg | Thr | Thr | Ala | His | Lys | Asp |
|   |   |   | 110 |   |   |   |   | 115 |   |   |   |   | 120 |   |   |

| Pro | Asn | Ala | Ile | Phe | Leu | Ser | Phe | Gln | His | Leu | Leu | Arg | Gly | Lys | Val |
|   |   | 125 |   |   |   |   | 130 |   |   |   |   | 135 |   |   |   |

| Arg | Phe | Leu | Met | Leu | Val | Gly | Gly | Ser | Thr | Leu | Cys | Val | Arg | Arg | Ala |
| 140 |   |   |   |   | 145 |   |   |   |   | 150 |   |   |   |   | 155 |

| Pro | Pro | Thr | Thr | Ala | Val | Pro | Ser | Arg | Thr | Ser | Leu | Val | Leu | Thr | Leu |
|   |   |   |   | 160 |   |   |   |   | 165 |   |   |   |   | 170 |   |

| Asn | Glu | Leu | Pro | Asn | Arg | Thr | Ser | Gly | Leu | Leu | Glu | Thr | Asn | Phe | Thr |
|   |   |   | 175 |   |   |   |   | 180 |   |   |   |   | 185 |   |   |

| Ala | Ser | Ala | Arg | Thr | Thr | Gly | Ser | Gly | Leu | Leu | Lys | Trp | Gln | Gln | Gly |
|   |   |   | 190 |   |   |   |   | 195 |   |   |   |   | 200 |   |   |

| Phe | Arg | Ala | Lys | Ile | Pro | Gly | Leu | Leu | Asn | Gln | Thr | Ser | Arg | Ser | Leu |
|   |   | 205 |   |   |   |   | 210 |   |   |   |   | 215 |   |   |   |

| | | | | | | | | | | | | | | | |
|---|---|---|---|---|---|---|---|---|---|---|---|---|---|---|---|
| Asp<br>220 | Gln | Ile | Pro | Gly | Tyr<br>225 | Leu | Asn | Arg | Ile | His<br>230 | Glu | Leu | Leu | Asn | Gly<br>235 |
| Thr | Arg | Gly | Leu | Phe<br>240 | Pro | Gly | Pro | Ser | Arg<br>245 | Arg | Thr | Leu | Gly | Ala<br>250 | Pro |
| Asp | Ile | Ser | Ser<br>255 | Gly | Thr | Ser | Asp | Thr<br>260 | Gly | Ser | Leu | Pro | Pro<br>265 | Asn | Leu |
| Gln | Pro | Gly<br>270 | Tyr | Ser | Pro | Ser | Pro<br>275 | Thr | His | Pro | Pro | Thr<br>280 | Gly | Gln | Tyr |
| Thr | Leu<br>285 | Phe | Pro | Leu | Pro | Pro<br>290 | Thr | Leu | Pro | Thr | Pro<br>295 | Val | Val | Gln | Leu |
| His<br>300 | Pro | Leu | Leu | Pro | Asp<br>305 | Pro | Ser | Ala | Pro | Thr<br>310 | Pro | Thr | Pro | Thr | Ser<br>315 |
| Pro | Leu | Leu | Asn | Thr<br>320 | Ser | Tyr | Thr | His | Ser<br>325 | Gln | Asn | Leu | Ser | Gln<br>330 | Glu |
| Gly | | | | | | | | | | | | | | | |